(12) United States Patent
Kandimalla et al.

(10) Patent No.: US 8,153,777 B2
(45) Date of Patent: Apr. 10, 2012

(54) MODULATION OF TOLL-LIKE RECEPTOR 5 EXPRESSION BY ANTISENSE OLIGONUCLEOTIDES

(75) Inventors: Ekambar Kandimalla, Southboro, MA (US); Mallikarjuna Putta, Burlington, MA (US); Lakshmi Bhagat, Framingham, MA (US); Daqing Wang, Bedford, MA (US); Dong Yu, Westboro, MA (US); Sudhir Agrawal, Shrewsbury, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 230 days.

(21) Appl. No.: 12/612,413

(22) Filed: Nov. 4, 2009

(65) Prior Publication Data

US 2010/0111937 A1    May 6, 2010

Related U.S. Application Data

(60) Provisional application No. 61/111,160, filed on Nov. 4, 2008.

(51) Int. Cl.
*C07H 21/04* (2006.01)
*C07H 21/02* (2006.01)
*A61K 48/00* (2006.01)
*A61K 39/395* (2006.01)
*C12N 15/63* (2006.01)

(52) U.S. Cl. .................. 536/24.5; 536/23.1; 536/24.31; 536/24.33; 514/44; 424/130.1; 435/320.1

(58) Field of Classification Search .................. None
See application file for complete search history.

(56) References Cited

U.S. PATENT DOCUMENTS

2006/0292572 A1    12/2006    Stuart et al.

FOREIGN PATENT DOCUMENTS

WO    WO 2007/047396 A2    4/2007

OTHER PUBLICATIONS

Scherer et al. (Nat. Biotechnol., 2003, 21(12), pp. 1457-1465).*
Akira, S. (2003) J. Biol. Chem. 278:38105.
Akira, S. et al. (2001) Nature Immunol. 2:675-680.
Alexopoulou, L. (2001) Nature 413:732-738.
Barrat and Coffman (2008) Immunol. Rev. 223:271-283.
Bock LC et al., Nature, 355:564-6, 1992.
Caricilli et al. (2008) J. Endocrinology 199:399.
Chaudhary et al. (1998) Blood 91: pp. 4020-4027.
Chen, Y., et al., Gene Ther. 8: 1024-1032 (2001).
Cook, D.N. et al. (2004) Nature Immunol. 5:975-979.
Diebold (2008) Adv. Drug Deliv. Rev. 60:813-823.
Diebold, S.S. et al. (2004) Science 303:1529-1531.
Duffy, K. et al. (2007) Cell Immunol. 248:103-114.
Gao et al. (2008) Semin. Immunopathol. 30:29-40.
Geller at al. (2008) Curr. Drug Dev. Tech. 5:29-38.
Gerwitz et al. (2001) J. Immunol. 167: pp. 1882-1885.
Gursel, I., et al. J. Immunol., 171: 1393-1400 (2003).
Hemmi H et al. (2002) Nat Immunol 3:196-200.
Hornung, V. et al., (2002) J. Immunol. 168:4531-4537.
Huang et al. (2005) Cancer Res. 65:5009-5014.
Huang et al. (2005) Invest. Opthal. Vis. Sci. 46:4209-4216.
Hyashi et al. (2001) Nature 410: pp. 1099-1103.
Iyer et al. (1995) Tetrahedron Asymmetry 6:1051-1054.
Jurk M et al., (2002) Nat Immunol 3:499.
Krieg, A. M. (2002) Annu. Rev. Immunol. 20:709.
Lee et al. (2008) Semin. Immunopathol. 30:3-9.
Lee J et al. (2003) Proc. Natl. Acad. Sci. USA 100:6646-6651.
Lenert, P. et al. (2003) DNA Cell Biol. 22(10):621-631.
Liew, F. et al. (2005) Nature 5:446-458.
Medzhitov, R. (2001) Nature Rev. Immunol. 1: 135-145.
Padmanabhan, K et al., J Biol Chem., 268(24):17651-4, 1993.
Papadimitraki et al. (2007) J. Autoimmun. 29: 310-318.
Patole, P. et al. (2005) J. Am. Soc. Nephrol. 16:3273-3280.
Ropert et al. (2008) Semin. Immunopathol. 30:41-51.
Salazar-Gonzalez and McSorley (2005) Immunol. Lett. 101: pp. 117-122.
Shirota, H., et al., J. Immunol., 173: 5002-5007 (2004).
Stein and Cheng, (1993) Science 261: pp. 1004-1012.
Stunz, L.L., Eur. J. Immunol. (2002) 32: 1212-1222.
Sun et al. (2007) Inflam. Allergy Drug Targets 6:223-235.
Tang et al. (1993) Nucleic Acids Res. 20:2729-2735.
Tobias & Curtiss (2008) Semin. Immunopathol. 30:23-27.
Trinchieri and Sher (2007) Nat. Rev. Immunol. 7:179-190.
Tse and Homer (2008) Semin. Immunopathol. 30:53-62.
Vijay-Kumar et al. (2008) Semin. Immunopathol. 30:pp. 11-21.

* cited by examiner

*Primary Examiner* — Amy Bowman
(74) *Attorney, Agent, or Firm* — McDonnell Boehnen Hulbert & Berghoff LLP

(57) ABSTRACT

Antisense oligonucleotide compounds, compositions and methods are provided for down regulating the expression of TLR5. The compositions comprise antisense oligonucleotides targeted to nucleic acids encoding TLR5. The compositions may also comprise antisense oligonucleotides targeted to nucleic acids encoding TLR5 in combination with other therapeutic and/or prophylactic compounds and/or compositions. Methods of using these compounds and compositions for down-regulating TLR5 expression and for prevention or treatment of diseases wherein modulation of TLR5 expression would be beneficial are provided.

23 Claims, 4 Drawing Sheets

NF-κB activation expressed as fold control (Mean+/-SD) in human TLR5 HEK293 cells

| Treatment | Antisense Alone | | | Agonist (1.25 µg/ml) Plus Antisense | | |
|---|---|---|---|---|---|---|
| | 1 µg/ml | 10 µg/ml | 100 µg/ml | 1 µg/ml | 10 µg/ml | 100 µg/ml |
| PBS | 1.00 ± 0.28 | | | 18.91±1.85 | | |
| 6 | 0.48±0.07 | 0.57±0.00 | 0.78±0.02 | 5.22±0.25 | 8.10±0.08 | 5.64±0.17 |
| 40 | 0.70±0.09 | 0.73±0.24 | 0.85±0.12 | 8.84±0.79 | 5.80±0.28 | 6.26±0.20 |
| 66 | 1.55±0.78 | 1.65±0.16 | 0.85±0.02 | 5.44±0.28 | 2.98±0.25 | 5.70±0.25 |
| 78 | 0.75±0.12 | 0.63±0.24 | 0.67±0.09 | 9.74±0.14 | 11.06±0.65 | 7.18±0.08 |
| 118 | 0.45±0.12 | 0.27±0.05 | 0.53±0.09 | 11.6±0.23 | 10.08±0.06 | 5.86±0.03 |
| 140 | 0.78±0.26 | 0.68±0.35 | 0.75±0.16 | 5.08±0.85 | 4.26±0.31 | 6.58±0.25 |
| 149 | 0.78±0.02 | 0.58±0.07 | 0.88±0.12 | 5.00±0.34 | 6.48±0.11 | 6.84±0.11 |

SEQ ID NO 174: 3431 bases
human toll-like receptor 5 (TLR5) mRNA (5'-3') (Genbank Accession No. NM 003268; VERSION NM 003268.4 GI: 124248535)

```
   1    GGTTTTCAGG AGCCCGAGCG AGGGCGCCGC TTTTGCGTCC GGGAGGAGCC AACCGTGGCG
  61    CAGGCGGCGC GGGGAGGCGT CCCAGAGTCT CACTCTGCCG CCCAGGCTGG ACTGCAGTGA
 121    CACAATCTCG GCTGACTGCA ACCACTGCCT CCAGGGTTCA AGCGATTCTC TTGCCTCAGC
 181    CTCCCAAGTA GCTGGGATTA CAGATTGATG TTCATGTTCC TGACACTACT ACAAGATTCA
 241    TACTCCTGAT GCTACTGACA ACGTGGCTTC TCCACAGTCA CCAAACCAGG GATGCTATAC
 301    TGGACTTCCC TACTCTCATC TGCTCCAGCC CCCTGACCTT ATAGTTGCCC AGCTTTCCTG
 361    GCAATTGACT TTGCCCATCA ATACACAGGA TTTAGCATCC AGGGAAGATG TCGGAGCCTC
 421    AGATGTTAAT TTTCTAATTG AGAATGTTGG CGCTGTCCGA ACCTGGAGAC AGGAAAACAA
 481    AAAGTCCTTT CTCCTGATTC ACCAAAAAAT AAAATACTGA CTACCATCAC TGTGATGAGA
 541    TTCCTATAGT CTCAGGAACT GAAGTCTTTA ACAACCAGG GACCCTCTGC CCCTAGAATA
 601    AGAACATACT GAAGTCCCT TCTGCTAGGA CAACGAGGAT CATGGGAGAC CACCTGGACC
 661    TTCTCCTAGG AGTGGTGCTC ATGGCCGGTC CTGTGTTTGG AATTCCTTCC TGCTCCTTTG
 721    ATGGCCGAAT AGCCTTTTAT CGTTTCTGCA ACCTCACCCA GGTCCCCCAG GTCCTCAACA
 781    CCACTGAGAG GCTCCTGCTG AGCTTCAACT ATATCAGGAC AGTCACTGCT TCATCCTTCC
 841    CCTTTCTGGA ACAGCTGCAG CTGCTGGAGC TCGGGAGCCA GTATACCCCC TTGACTATTG
 901    ACAAGGAGGC CTTCAGAAAC CTGCCCAACC TTAGAATCTT GGACCTGGGA AGTAGTAAGA
 961    TATACTTCTT GCATCCAGAT GCTTTTCAGG GACTGTTCCA TCTGTTTTGAA CTTAGACTGT
1021    ATTTCTGTGG TCTCTCTGAT GCTGTATTGA AAGATGGTTA TTTCAGAAAT TTAAAGGCTT
1081    TAACTCGCTT GGATCTATCC AAAAATCAGA TTCGTAGCCT TTACCTTCAT CCTTCATTTG
1141    GGAAGTTGAA TTCCTTAAAG TCCATAGATT TTTCCTCCAA CCAAATATTC CTTGTATGTG
1201    AACATGAGCT CGAGCCCCTA CAAGGGAAAA CGCTCTCCTT TTTTAGCCTC GCAGCTAATA
1261    GCTTGTATAG CAGAGTCTCA GTGGACTGGG GAAAATGTAT GAACCCATTC AGAAACATGG
1321    TGCTGGAGAT ACTAGATGTT TCTGGAAATG GCTGGACAGT GGACATCACA GGAAACTTTA
1381    GCAATGCCAT CAGCAAAAGC CAGGCCTTCT CTTTGATTCT TGCCCACCAC ATCATGGGTG
1441    CCGGGTTTGG CTTCCATAAC ATCAAAGATC CTGACCAGAA CACATTTGCT GGCCTGGCCA
1501    GAAGTTCAGT GAGACACCTG GATCTTTCAC ATGGGTTTGT CTTCTCCCTG AACTCACGAG
1561    TCTTTGAGAC ACTCAAGGAT TTGAAGGTTC TGAACCTTGC CTACAACAAG ATAAATAAGA
1621    TTGCAGATGA AGCATTTTAC GGACTTGACA ACCTCCAAGT TCTCAATTTG TCATATAACC
1681    TTCTGGGGGA ACTTTACAGT TCGAATTTCT ATGGACTACC TAAGGTAGCC TACATTGATT
1741    TGCAAAAGAA TCACATTGCA ATAATTCAAG ACCAAACATT CAAATTCCTG GAAAAATTAC
1801    AGACCTTGGA TCTCCGAGAC AATGCTCTTA CAACCATTCA TTTTATTCCA AGCATACCCG
1861    ATATCTTCTT GAGTGGCAAT AAAACTAGTGA CTTTGCCAAA GATCAACCTT ACAGCGAACC
1921    TCATCCACTT ATCAGAAAAC AGGCTAGAAA ATCTAGATAT TCTCTACTTT CTCCTACGGG
1981    TACCTCATCT CCAGATTCTC ATTTTAAATC AAAATCGCTT CTCCTCCTGT AGTGGAGATC
2041    AAACCCCTTC AGAGAATCCC AGCTTAGAAC AGCTTTTCCT TGGAGAAAAT ATGTTGCAAC
2101    TTGCCTGGGA AACTGAGCTC TGTTGGGATG TTTTTGAGGG ACTTTCTCAT CTTCAAGTTC
2161    TGTATTTGAA TCATAACTAT CTTAATTCCC TTCCACCAGG AGTATTTAGC CATCTGACTG
2221    CATTAAGGGG ACTAAGCCTC AACTCCAACA GGCTGACAGT TCTTTCTCAC AATGATTTAC
2281    CTGCTAATTT AGAGATCCTG GACATATCCA GGAACCAGCT CCTAGCTCCT AATCCTGATG
2341    TATTTGTATC ACTTAGTGTC TTGGATATAA CTCATAACAA GTTCATTTGT GAATGTGAAC
2401    TTAGCACTTT TATCAATTGG CTTAATCACA CCAATGTCAC TATAGCTGGG CCTCCTGCAG
2461    ACATATATTG TGTGTACCCT GACTCGTTCT CTGGGGTTTC CCTCTTCTCT CTTTCCACGG
2521    AAGGTTGTGA TGAAGAGGAA GTCTTAAAGT CCCTAAAGTT CTCCCTTTTC ATTGTATGCA
2581    CTGTCACTCT GACTCTGTTC CTCATGACCA TCCTCACAGT CACAAAGTTC CGGGGCTTCT
2641    GTTTTATCTG TTATAAGACA GCCCAGAGAC TGGTGTTCAA GGACCATCCC CAGGGCACAG
2701    AACCTGATAT GTACAAATAT GATGCCTATT TGTGCTTCAG CAGCAAAGAC TTCACATGGG
2761    TGCAGAATGC TTTGCTCAAA CACCTGGACA CTCAATACAG TGACCAAAAC AGATTCAACC
2821    TGTGCTTTGA AGAAAGAGAC TTTGTCCCAG GAGAAAACCG CATTGCCAAT ATCCAGGATG
2881    CCATCTGGAA CAGTAGAAAG ATCGTTTGTC TTGTGAGCAG ACACTTCCTT AGAGATGGCT
2941    GGTGCCTTGA AGCCTTCAGT TATGCCCAGG GCAGGTGCTT ATCTGACCTT AACAGTGCTC
```

```
3001  TCATCATGGT GGTGGTTGGG TCCTTGTCCC AGTACCAGTT GATGAAACAT CAATCCATCA
3061  GAGGCTTTGT ACAGAAACAG CAGTATTTGA GGTGGCCTGA GGATCTCCAG GATGTTGGCT
3121  GGTTTCTTCA TAAACTCTCT CAACAGATAC TAAAGAAAGA AAAAGAAAAG AAGAAAGACA
3181  ATAACATTCC GTTGCAAACT GTAGCAACCA TCTCCTAATC AAAGGAGCAA TTTCCAACTT
3241  ATCTCAAGCC ACAAATAACT CTTCACTTTG TATTTGCACC AAGTTATCAT TTTGGGGTCC
3301  TCTCTGGAGG TTTTTTTTTT CTTTTTGCTA CTATGAAAAC AACATAAATC TCTCAATTTT
3361  CGTATCAACA CCATGTTCTG TCTCACTAAC CTCCAAATGG AAAATAATAG ATCTAGAAAA
3421  TTGCAACTGC C
```

Figure 3 (con't.)

MODULATION OF TOLL-LIKE RECEPTOR 5 EXPRESSION BY ANTISENSE OLIGONUCLEOTIDES

This application claims the benefit of priority from U.S. Provisional Patent Application No. 61/111,160, filed on Nov. 4, 2008, the disclosure of which is explicitly incorporated by reference herein.

BACKGROUND OF THE INVENTION

1. Field of the Invention

The present invention relates to Toll-Like Receptor 5 (TLR5). In particular, the invention relates to antisense oligonucleotides that specifically hybridize with nucleic acids encoding TLR5, thus modulating TLR5 expression and activity, and their use in treating or preventing diseases associated with TLR5 or wherein modulation of TLR5 expression would be beneficial.

2. Summary of the Related Art

Toll-like receptors (TLRs) are present on many cells of the immune system and have been shown to be involved in the innate immune response (Hornung, V. et al., (2002) J. Immunol. 168:4531-4537). TLRs are a key means by which mammals recognize and mount an immune response to foreign molecules and also provide a means by which the innate and adaptive immune responses are linked (Akira, S. et al. (2001) Nature Immunol. 2:675-680; Medzhitov, R. (2001) Nature Rev. Immunol. 1:135-145). In vertebrates, this family consists of at least 11 proteins called TLR1 to TLR11, which are known to recognize pathogen associated molecular patterns (PAMP) from bacteria, fungi, parasites and viruses and induce an immune response mediated by a number of transcription factors.

Some TLRs are located on the cell surface to detect and initiate a response to extracellular pathogens and other TLRs are located inside the cell to detect and initiate a response to intracellular pathogens. Table 1 provides a representation of TLRs, the known agonists therefore and the cell types known to contain the TLR (Diebold, S. S. et al. (2004) Science 303:1529-1531; Liew, F. et al. (2005) Nature 5:446-458; Hemmi H et al. (2002) Nat Immunol 3:196-200; Jurk M et al., (2002) Nat Immunol 3:499; Lee J et al. (2003) Proc. Natl. Acad. Sci. USA 100:6646-6651); (Alexopoulou, L. (2001) Nature 413:732-738).

TABLE 1

| TLR Molecule | Agonist | Cell Types Containing Receptor |
|---|---|---|
| Cell Surface TLRs: | | |
| TLR2 | bacterial lipopeptides | Monocytes/macrophages<br>Myeloid dendritic cells<br>Mast cells |
| TLR4 | gram negative bacteria | Monocytes/macrophages<br>Myeloid dendritic cells<br>Mast cells<br>Intestinal epithelium |
| TLR5 | motile bacteria | Monocyte/macrophages<br>Dendritic cells<br>Intestinal epithelium |
| TLR6 | gram positive bacteria | Monocytes/macrophages<br>Mast cells<br>B lymphocytes |
| Endosomal TLRs: | | |
| TLR3 | double stranded RNA viruses | Dendritic cells<br>B lymphocytes |

TABLE 1-continued

| TLR Molecule | Agonist | Cell Types Containing Receptor |
|---|---|---|
| TLR7 | single stranded RNA viruses; RNA-immunoglobulin complexes | Monocytes/macrophages<br>Plasmacytoid dendritic cells<br>B lymphocytes |
| TLR8 | single stranded RNA viruses; RNA-immunoglobulin complexes | Monocytes/macrophages<br>Dendritic cells<br>Mast cells |
| TLR9 | DNA containing unmethylated "CpG" motifs; DNA-immunoglobulin complexes | Monocytes/macrophages<br>Plasmacytoid dendritic cells<br>B lymphocytes |

The signal transduction pathway mediated by the interaction between a ligand and a TLR is shared among most members of the TLR family and involves a toll/IL-1 receptor (TIR domain), the myeloid differentiation marker 88 (MyD88), IL-1R-associated kinase (IRAK), interferon regulating factor (IRF), TNF-receptor-associated factor (TRAF), TGFβ-activated kinase1, IκB kinases, IκB, and NF-κB (see for example: Akira, S. (2003) J. Biol. Chem. 278:38105 and Geller at al. (2008) Curr. Drug Dev. Tech. 5:29-38). More specifically, for TLRs 1, 2, 4, 5, 6, 7, 8, 9 and 11, this signaling cascade begins with a PAMP ligand interacting with and activating the membrane-bound TLR, which exists as a homo-dimer in the endosomal membrane or the cell surface. Following activation, the receptor undergoes a conformational change to allow recruitment of the TIR domain containing protein MyD88, which is an adapter protein that is common to all TLR signaling pathways except TLR3. MyD88 recruits IRAK4, which phosphorylates and activates IRAK1. The activated IRAK1 binds with TRAF6, which catalyzes the addition of polyubiquitin onto TRAF6. The addition of ubiquitin activates the TAK/TAB complex, which in turn phosphorylates IRFs, resulting in NF-κB release and transport to the nucleus. NF-κB in the nucleus induces the expression of proinflammatory genes (see for example, Trinchieri and Sher (2007) Nat. Rev. Immunol. 7:179-190).

The selective localization of TLRs and the signaling generated therefrom, provides some insight into their role in the immune response. The immune response involves both an innate and an adaptive response based upon the subset of cells involved in the response. For example, the T helper (Th) cells involved in classical cell-mediated functions such as delayed-type hypersensitivity and activation of cytotoxic T lymphocytes (CTLs) are Th1 cells. This response is the body's innate response to antigen (e.g. viral infections, intracellular pathogens, and tumor cells), and results in a secretion of IFN-gamma and a concomitant activation of CTLs. TLR5 is known to localize on the cell membrane and is activated by flagellin, which is a principal component of bacterial flagella and serves as a virulence factor recognized by the innate immune system in plants, insects, and mammals (Hyashi et al. (2001) Nature 410:1099-1103). This ability of TLR5 to respond to flagellin demonstrates TLR5's ability to generate an immune respond to a broad group of motile pathogens.

As a result of their involvement in regulating an inflammatory response, TLRs have been shown to play a role in the pathogenesis of many diseases, including autoimmunity, infectious disease and inflammation (Papadimitraki et al. (2007) J. Autoimmun. 29: 310-318; Sun et al. (2007) Inflam. Allergy Drug Targets 6:223-235; Diebold (2008) Adv. Drug Deliv. Rev. 60:813-823; Cook, D. N. et al. (2004) Nature Immunol. 5:975-979; Tse and Horner (2008) Semin. Immunopathol. 30:53-62; Tobias & Curtiss (2008) Semin. Immunopathol. 30:23-27; Ropert et al. (2008) Semin. Immunopathol. 30:41-51; Lee et al. (2008) Semin. Immunopathol. 30:3-9; Gao et al. (2008) Semin. Immunopathol. 30:29-40; Vijay-Kumar et al. (2008) Semin. Immunopathol. 30:11-21). While activation of TLRs is involved in mounting an immune response, an uncontrolled or undesired stimulation of the immune system through TLRs may exacerbate certain diseases in immune compromised subjects or may cause unwanted immune stimulation. Thus, down-regulating TLR expression and/or activity may provide a useful means for disease intervention.

To date, investigative strategies aimed selectively at inhibiting TLR activity have involved small molecules (WO/2005/007672), antibodies (see for example: Duffy, K. et al. (2007) Cell Immunol. 248:103-114), catalytic RNAi technologies (e.g. small inhibitory RNAs), certain antisense molecules (Caricilli et al. (2008) J. Endocrinology 199:399), and competitive inhibition with modified or methylated oligonucleotides (see for example: Kandimalla et al. US2008/0089883; Banat and Coffman (2008) Immunol. Rev. 223:271-283). For example, chloroquine and hydroxychloroquine have been shown to block endosomal-TLR signaling by down-regulating the maturation of endosomes (Krieg, A. M. (2002) Annu Rev. Immunol. 20:709). Also, Huang et al. have shown the use of TLR4 siRNA to reverse the tumor-mediated suppression of T cell proliferation and natural killer cell activity (Huang et al. (2005) Cancer Res. 65:5009-5014), and the use of TLR9 siRNA to prevent bacterial-induced inflammation of the eye (Huang et al. (2005) Invest. Opthal. Vis. Sci. 46:4209-4216).

Additionally, several groups have used synthetic oligodeoxynucleotides having two triplet sequences, a proximal "CCT" triplet and a distal "GGG" triplet, a poly "G" (e.g. "GGGG" or "GGG") or "GC" sequences that interact with certain intracellular proteins, resulting in the inhibition of TLR signaling and the concomitant production and release of pro-inflammatory cytokines (see for example: Lenert, P. et al. (2003) DNA Cell Biol. 22(10):621-631; Patole, P. et al. (2005) J. Am. Soc. Nephrol. 16:3273-3280), Gursel, I., et al. (J. Immunol., 171: 1393-1400 (2003), Shirota, H., et al., J. Immunol., 173: 5002-5007 (2004), Chen, Y., et al., Gene Ther. 8: 1024-1032 (2001); Stunz, L. L., Eur. J. Immunol. (200) 32: 1212-1222; Kandimalla et al. WO2007/7047396). However, oligonucleotides containing guanosine strings have been shown to form tetraplex structures, act as aptamers and inhibit thrombin activity (Bock L C et al., Nature, 355:564-6, 1992; Padmanabhan, K et al., J Biol. Chem., 268(24):17651-4, 1993). Thus, the utility of these inhibitory oligodeoxynucleotide molecules may not be achievable in patients.

A potential approach to inhibiting, suppressing or down regulating expression of TLRs is antisense technology. The history of developing antisense technology indicates that while designing and testing antisense oligonucleotides that hybridize to target RNA is a relatively straight forward exercise, only a few antisense oligonucleotides work as intended and optimization of antisense oligonucleotides that have true potential as clinical candidates is not predictable. One skilled in the art would recognize that when optimizing antisense oligonucleotides, conceiving the correct oligonucleotide sequence and length, and utilizing the appropriate nucleic acid and oligonucleotide chemistries are not readily apparent. However, formulating these components is crucial to the utility of any antisense oligonucleotide (Stein and Cheng, 1993, Science 261: 1004-1012). One skilled in the art would further recognize that without conceiving the correct sequence, the correct length, and utilizing the appropriate nucleic acid and oligonucleotide chemistries, the antisense oligonucleotide can have off-target effects and can cause, among other things, the molecule to be unstable, inactive, non-specific, and toxic. As a result of the unpredictable nature of antisense oligonucleotides, to date only one antisense oligonucleotide has received approval for use in humans, and no antisense oligonucleotides are currently being marketed for human use.

Accordingly, there exists a need in the field for optimized antisense oligonucleotides that most efficiently down-regulate or inhibit gene expression. In particular, there exists a need in the field for antisense oligonucleotides that down-regulate TLR5 expression and that are stable, active, target specific, non-toxic, and do not activate an innate immune response. A molecule with such characteristics would overcome the problems that have previously prevented antisense oligonucleotides from being developed.

BRIEF SUMMARY OF THE INVENTION

The present invention is directed to, among other things, optimized synthetic antisense oligonucleotides that are targeted to a nucleic acid encoding TLR5 and that efficiently inhibit the expression of TLR5 through inhibition of mRNA translation and/or through an RNase H mediated mechanism.

In a first aspect, optimized antisense oligonucleotides according to the invention include those having SEQ ID NOs: 6, 40, 66, 78, 118, 140 or 149.

In another aspect, the invention provides a composition comprising at least one optimized antisense oligonucleotide according to the invention and a physiologically acceptable carrier, diluent or excipient.

In another aspect, the invention provides a method of inhibiting TLR5 expression. In this method, an oligonucleotide or multiple oligonucleotides of the invention are specifically contacted or hybridized with TLR5 mRNA either in vitro or in a cell.

In another aspect, the invention provides methods for inhibiting the expression of TLR5 in a mammal, particularly a human, such methods comprising administering to the mammal a compound or composition according to the invention.

In another aspect, the invention provides a method for inhibiting a TLR5-mediated immune response in a mammal, the method comprising administering to the mammal a TLR5 antisense oligonucleotide according to the invention in a pharmaceutically effective amount.

In another aspect, the invention provides a method for therapeutically treating a mammal having a disease mediated by TLR5, such method comprising administering to the mammal, particularly a human, a TLR5 antisense oligonucleotide of the invention, or a composition thereof, in a pharmaceutically effective amount.

In another aspect, the invention provides methods for preventing a disease or disorder in a mammal, particularly a human, at risk of contracting or developing a disease or disorder mediated by TLR5. Such methods comprise administering to the mammal an antisense oligonucleotide according to the invention, or a composition thereof, in a prophylactically effective amount.

In another aspect, the invention provides a method for inhibiting TLR5 expression and activity in a mammal, comprising administering to the mammal an antisense oligonucleotide complementary to TLR5 mRNA and an antagonist of TLR5 protein, a kinase inhibitor or an inhibitor of signal transduction and transcription (STAT) protein.

The subject oligonucleotides and methods disclosed herein are also useful for examining the function of the TLR5 gene in a cell or in a control mammal or in a mammal afflicted with a disease or disorder associated with TLR5 or immune stimulation through TLR5. The cell or mammal is administered the oligonucleotide, and the expression of TLR5 mRNA or protein is examined.

BRIEF DESCRIPTION OF THE DRAWINGS

FIG. 2 demonstrates that exemplary human TLR5 antisense oligonucleotides according to the invention are not immunostimulatory (Antisense Alone). FIG. 2 also demonstrates the ability of exemplary oligonucleotides according to the invention to inhibit TLR5 expression and activation in HEK293 cells that were cultured and treated according to Example 2 (Agonist Plus AS).

FIG. 3 shows the nucleotide sequence of human TLR5 mRNA [SEQ ID NO: 174] (Genbank Accession No. NM 003268).

DETAILED DESCRIPTION

Figure 1:
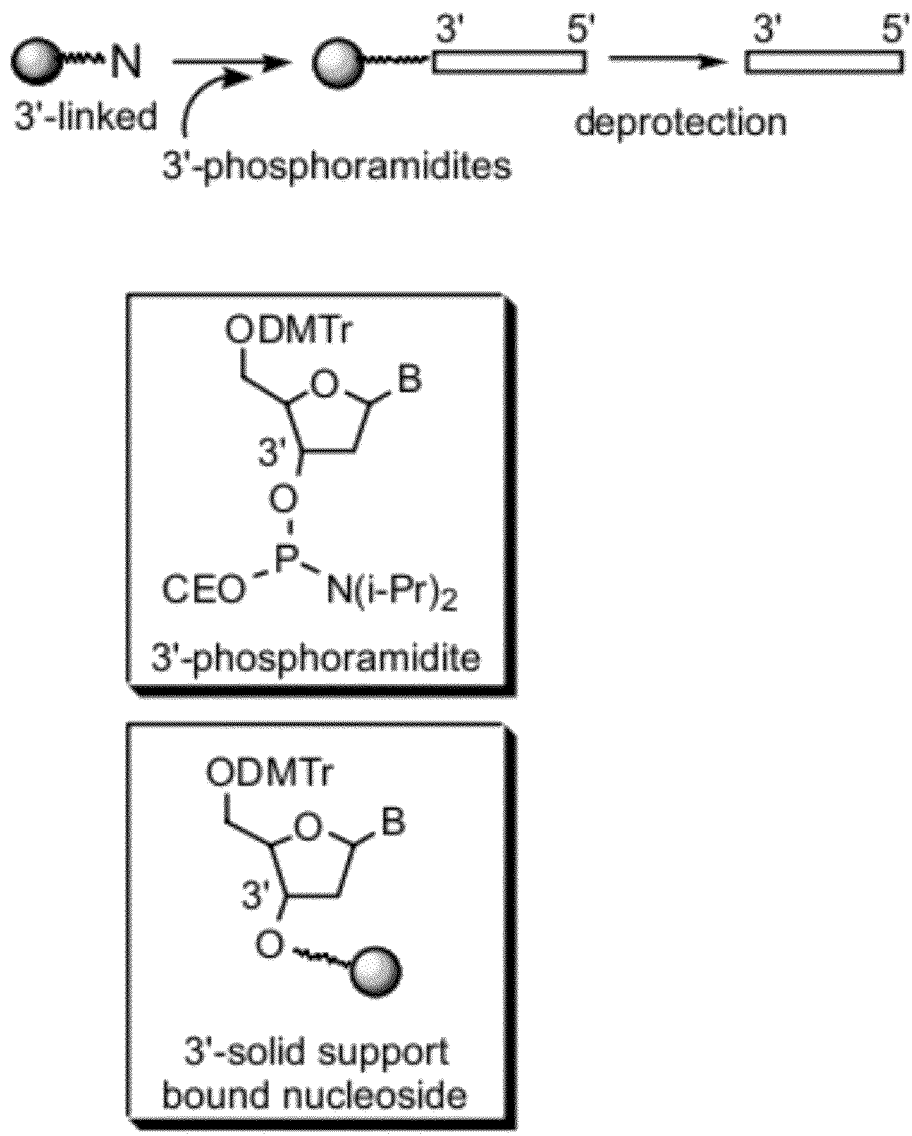
FIG. 1 is a synthetic scheme for the linear synthesis of antisense oligonucleotides of the invention. DMTr=4,4'-dimethoxytrityl; CE=cyanoethyl.

The invention relates to optimized TLR5 antisense oligonucleotides, compositions comprising such oligonucleotides, and methods of their use for inhibiting or suppressing a TLR5-mediated immune response. More specifically, the antisense oligonucleotides according to the invention are stable, active, target specific, non-toxic, and do not activate an innate immune response. Pharmaceutical and other compositions comprising the compounds according to the invention are also provided. Further provided are methods of downregulating the expression of TLR2 in cells or tissues comprising contacting said cells or tissues with one or more of the antisense compounds or compositions of the invention alone or in combination with other prophylactic or therapeutic compositions.

Specifically, the invention provides antisense oligonucleotides that are designed to be complementary to a genomic region or an RNA molecule transcribed therefrom. These TLR5 antisense oligonucleotides are stable, target specific, and have unique sequences that result in the molecule being maximally effective at inhibiting or suppressing TLR5-mediated signaling in response to endogenous and/or exogenous TLR5 ligands or TLR5 agonists The TLR5 antisense oligonucleotides according to the invention inhibit immune responses induced by natural or artificial TLR5 agonists in various cell types and in various in vitro and in vivo experimental models. As such, the antisense compositions according to the invention are useful as tools to study the immune system, as well as to compare the immune systems of various mammals, such as humans and mice.

Further provided are methods of treating a mammal, particularly a human, having, suspected of having, or being prone to develop a disease or condition associated with TLR5 activation by administering a therapeutically or prophylactically effective amount of one or more of the antisense compounds or compositions of the invention. Since TLR5 has been identified to recognize and respond to flagellin from both Gram-positive and Gram-negative bacteria, triggering proinflammatory as well as adaptive immune responses (Gerwitz et al. (2001) J. Immunol. 167:1882-1885; Salazar-Gonzalez and McSorley (2005) Immunol. Lett. 101:117-122), the optimized antisense oligonucleotides and compositions according to the invention can be used for immunotherapy applications such as, but not limited to, treatment of cancer, autoimmune disorders, asthma, respiratory allergies, food allergies, skin allergies, systemic lupus erythematosus (SLE), arthritis, pleurisy, chronic infections, inflammatory diseases, inflammatory bowel syndrome, sepsis, malaria, and bacteria, parasitic, and viral infections in adult and pediatric human and veterinary applications. In addition, TLR5 antisense oligonucleotides of the invention are useful in preventing and/or treating various diseases, either alone, in combination with or when co-administered with other drugs or prophylactic or therapeutic compounds or compositions, for example, DNA vaccines, antigens, antibodies, and allergens; and in combination with chemotherapeutic agents (both traditional chemotherapy and modern targeted therapies) and/or TLR5 antagonists for prevention and treatment of diseases. In addition, TLR5 antisense oligonucleotides according to the invention are useful in combination with compounds, compositions or drugs that have unwanted TLR5-medicated immune stimulatory properties.

The objects of the present invention, the various features thereof, as well as the invention itself may be more fully understood from the following description, when read together with the accompanying drawings in which the following terms have the ascribed meaning.

The term "2'-O-substituted" means substitution of the 2' position of the pentose moiety with an —O— lower alkyl group containing 1-6 saturated or unsaturated carbon atoms (for example, but not limited to, 2'-O-methyl), or with an —O-aryl or allyl group having 2-6 carbon atoms, wherein such alkyl, aryl or allyl group may be unsubstituted or may be substituted, (for example, with 2'-O-ethoxy-methyl, halo, hydroxy, trifluoromethyl, cyano, nitro, acyl, acyloxy, alkoxy, carboxyl, carbalkoxyl, or amino groups); or with a hydroxy, an amino or a halo group, but not with a 2'-H group. In some embodiments the oligonucleotides of the invention include four or five 2'-O-alky ribonucleotides at their 5' terminus, and/or four or five 2'-O-alky ribonucleotides at their 3' terminus. In exemplary embodiments, the nucleotides of the synthetic oligonucleotides are linked by at least one phosphorothioate internucleotide linkage. The phosphorothioate linkages may be mixed Rp and Sp enantiomers, or they may be stereoregular or substantially stereoregular in either Rp or Sp form (see Iyer et al. (1995) Tetrahedron Asymmetry 6:1051-1054).

The term "3'", when used directionally, generally refers to a region or position in a polynucleotide or oligonucleotide 3' (toward the 3' end of the nucleotide) from another region or position in the same polynucleotide or oligonucleotide.

The term "5'", when used directionally, generally refers to a region or position in a polynucleotide or oligonucleotide 5' (toward the 5' end of the nucleotide) from another region or position in the same polynucleotide or oligonucleotide.

The term "about" generally means that the exact number is not critical. Thus, oligonucleotides having one or two fewer nucleoside residues, or from one to several additional nucleoside residues are contemplated as equivalents of each of the embodiments described above.

The term "agonist" generally refers to a substance that binds to a receptor of a cell and induces a response. An agonist often mimics the action of a naturally occurring substance such as a ligand.

The term "antagonist" generally refers to a substance that attenuates the effects of an agonist.

The term "airway inflammation" generally includes, without limitation, inflammation in the respiratory tract caused by allergens, including asthma.

The term "allergen" generally refers to an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule.

The term "allergy" generally includes, without limitation, food allergies, respiratory allergies and skin allergies.

The term "antigen" generally refers to a substance that is recognized and selectively bound by an antibody or by a T cell antigen receptor. Antigens may include but are not limited to peptides, proteins, nucleosides, nucleotides and combinations thereof. Antigens may be natural or synthetic and generally induce an immune response that is specific for that antigen.

The term "autoimmune disorder" generally refers to disorders in which "self" antigen undergo attack by the immune system. Such term includes, without limitation, lupus erythematosus, multiple sclerosis, type I diabetes mellitus, irritable bowel syndrome, Chron's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjören's syndrome, temporal arteritis ("giant cell arteritis"), vasculitis, vitiligo, vulvodynia and Wegener's granulomatosis autoimmune asthma, septic shock and psoriasis.

The term "cancer" generally refers to, without limitation, any malignant growth or tumor caused by abnormal or uncontrolled cell proliferation and/or division. Cancers may occur in humans and/or mammals and may arise in any and all tissues. Treating a patient having cancer may include administration of a compound, pharmaceutical formulation or vaccine according to the invention such that the abnormal or uncontrolled cell proliferation and/or division, or metastasis is affected.

The term "carrier" generally encompasses any excipient, diluent, filler, salt, buffer, stabilizer, solubilizer, oil, lipid, lipid containing vesicle, microspheres, liposomal encapsulation, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, for example, *Remington's Pharmaceutical Sciences,* 18th Edition, ed. A. Gennaro, Mack Publishing Co., Easton, Pa., 1990.

The terms "co-administration" or "co-administered" generally refers to the administration of at least two different substances sufficiently close in time to modulate an immune response. Co-administration refers to simultaneous administration, as well as temporally spaced order of up to several days apart, of at least two different substances in any order, either in a single dose or separate doses.

The term "in combination with" generally means administering a compound according to the invention and another agent useful for treating the disease or condition that does not abolish TLR5 antisense activity of the compound in the course of treating a patient. Such administration may be done in any order, including simultaneous administration, as well as temporally spaced order from a few seconds up to several days apart. Such combination treatment may also include more than a single administration of the compound according to the invention and/or independently the other agent. The administration of the compound according to the invention and the other agent may be by the same or different routes.

The terms "individual" or "subject" or "patient" or "vertebrate" generally refers to a mammal, such as a human.

The terms "inhibit" or "suppress" or "down-regulate", when used in reference to expression, generally refer to a decrease in a response or qualitative difference in a response, which could otherwise arise from eliciting and/or stimulation of a response.

The term "kinase inhibitor" generally refers to molecules that antagonize or inhibit phosphorylation-dependent cell signaling and/or growth pathways in a cell. Kinase inhibitors may be naturally occurring or synthetic and include small molecules that have the potential to be administered as oral therapeutics. Kinase inhibitors have the ability to rapidly and specifically inhibit the activation of the target kinase molecules. Protein kinases are attractive drug targets, in part because they regulate a wide variety of signaling and growth pathways and include many different proteins. As such, they have great potential in the treatment of diseases involving kinase signaling, including cancer, cardiovascular disease, inflammatory disorders, diabetes, macular degeneration and neurological disorders. Examples of kinase inhibitors include sorafenib (Nexavar®), Sutent®, dasatinib, Dasatinib™, Zactima™, Tykerb™ and STI571.

The term "linear synthesis" generally refers to a synthesis that starts at one end of an oligonucleotide and progresses linearly to the other end. Linear synthesis permits incorporation of either identical or non-identical (in terms of length, base composition and/or chemical modifications incorporated) monomeric units into an oligonucleotide.

The term "mammal" is expressly intended to include warm blooded, vertebrate animals, including, without limitation, humans, non-human primates, rats, mice, cats, dogs, horses, cattle, cows, pigs, sheep and rabbits.

The term "nucleoside" generally refers to compounds consisting of a sugar, usually ribose or deoxyribose, and a purine or pyrimidine base.

The term "nucleotide" generally refers to a nucleoside comprising a phosphorous-containing group attached to the sugar.

The term "modified nucleoside" generally is a nucleoside that includes a modified heterocyclic base, a modified sugar moiety, or any combination thereof. In some embodiments, the modified nucleoside is a non-natural pyrimidine or purine nucleoside, as herein described. For purposes of the invention, a modified nucleoside, a pyrimidine or purine analog or non-naturally occurring pyrimidine or purine can be used interchangeably and refers to a nucleoside that includes a non-naturally occurring base and/or non-naturally occurring sugar moiety. For purposes of the invention, a base is considered to be non-natural if it is not guanine, cytosine, adenine, thymine or uracil and a sugar is considered to be non-natural if it is not β-ribo-furanoside or 2'-deoxyribo-furanoside.

The term "modified oligonucleotide" as used herein describes an oligonucleotide in which at least two of its nucleotides are covalently linked via a synthetic linkage, i.e., a linkage other than a phosphodiester linkage between the 5' end of one nucleotide and the 3' end of another nucleotide in which the 5' nucleotide phosphate has been replaced with any number of chemical groups. The term "modified oligonucleotide" also encompasses oligonucleotides having at least one nucleotide with a modified base and/or sugar, such as a 2'-O-substituted, a 5-methylcytosine and/or a 3'-O-substituted ribonucleotide.

The term "nucleic acid" encompasses a genomic region or an RNA molecule transcribed therefrom. In some embodiments, the nucleic acid is mRNA.

The term "nucleotidic linkage" generally refers to a chemical linkage to join two nucleosides through their sugars (e.g. 3'-3', 2'-3',2'-5', 3'-5', 5'-5') consisting of a phosphorous atom and a charged, or neutral group (e.g., phosphodiester, phosphorothioate, phosphorodithioate or methylphosphonate) between adjacent nucleosides.

The term "oligonucleotide" refers to a polynucleoside formed from a plurality of linked nucleoside units. The nucleoside units may be part of viruses, bacteria, cell debris or oligonucleotide-based compositions (for example, siRNA and microRNA). Such oligonucleotides can also be obtained from existing nucleic acid sources, including genomic or cDNA, but are preferably produced by synthetic methods. In certain embodiments each nucleoside unit includes a heterocyclic base and a pentofuranosyl, trehalose, arabinose, 2'-deoxy-2'-substituted nucleoside, 2'-deoxy-2'-substituted arabinose, 2'-O-substitutedarabinose or hexose sugar group. The nucleoside residues can be coupled to each other by any of the numerous known internucleoside linkages. Such internucleoside linkages include, without limitation, phosphodiester, phosphorothioate, phosphorodithioate, methylphosphonate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide-based compound" also encompasses polynucleosides having one or more stereospecific internucleoside linkage (e.g., ($R_p$)- or ($S_p$)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain exemplary embodiments, these internucleoside linkages may be phosphodiester, phosphorothioate or phosphorodithioate linkages, or combinations thereof.

The term "complementary to a genomic region or an RNA molecule transcribed therefrom" is intended to mean an oligonucleotide that binds to the nucleic acid sequence under physiological conditions, for example, by Watson-Crick base pairing (interaction between oligonucleotide and single-stranded nucleic acid) or by Hoogsteen base pairing (interaction between oligonucleotide and double-stranded nucleic acid) or by any other means, including in the case of an oligonucleotide, binding to RNA and causing pseudoknot formation. Binding by Watson-Crick or Hoogsteen base pairing under physiological conditions is measured as a practical matter by observing interference with the function of the nucleic acid sequence.

The term "peptide" generally refers to polypeptides that are of sufficient length and composition to affect a biological response, for example, antibody production or cytokine activity whether or not the peptide is a hapten. The term "peptide" may include modified amino acids (whether or not naturally or non-naturally occurring), where such modifications include, but are not limited to, phosphorylation, glycosylation, pegylation, lipidization and methylation.

The term "pharmaceutically acceptable" means a non-toxic material that does not interfere with the effectiveness of a compound according to the invention or the biological activity of a compound according to the invention.

The term "physiologically acceptable" refers to a non-toxic material that is compatible with a biological system such as a cell, cell culture, tissue, or organism. Preferably, the biological system is a living organism, such as a mammal, particularly a human.

The term "prophylactically effective amount" generally refers to an amount sufficient to prevent or reduce the development of an undesired biological effect.

The terms "therapeutically effective amount" or "pharmaceutically effective amount" generally refers to an amount sufficient to affect a desired biological effect, such as a beneficial result, including, without limitation, prevention, diminution, amelioration or elimination of signs or symptoms of a disease or disorder. Thus, the total amount of each active component of the pharmaceutical composition or method is sufficient to show a meaningful patient benefit, for example, but not limited to, healing of chronic conditions characterized by immune stimulation. Thus, a "pharmaceutically effective amount" will depend upon the context in which it is being administered. A pharmaceutically effective amount may be administered in one or more prophylactic or therapeutic administrations. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "treatment" generally refers to an approach intended to obtain a beneficial or desired result, which may include alleviation of symptoms, or delaying or ameliorating a disease progression.

The invention provides antisense oligonucleotides that are complementary to a nucleic acid that is specific for human TLR5 (SEQ ID NO: 174). The antisense oligonucleotides according to the invention are optimized with respect to (i) the targeted region of the TLR5 mRNA coding sequence, the 5' untranslated region or the 3' untranslated region, (ii) their chemical modification(s), or (iii) both. In some embodiments, the compounds are complementary to a region within nucleotides 642 through 3218 of the coding region, or nucleotides 1-641 of the 5' untranslated region, or 3219-3431 of the 3' untranslated region of TLR5 mRNA (SEQ ID NO: 174).

Antisense oligonucleotides according to the invention are useful in treating and/or preventing diseases wherein inhibiting a TLR5-mediated immune response would be beneficial. TLR5-targeted antisense oligonucleotides according to the invention that are useful include, but are not limited to, antisense oligonucleotides comprising naturally occurring nucleotides, modified nucleotides, modified oligonucleotides and/or backbone modified oligonucleotides. However, antisense oligonucleotides that inhibit the translation of mRNA encoded proteins may produce undesired biological effects, including but not limited to insufficiently active antisense oligonucleotides, inadequate bioavailability, suboptimal pharmacokinetics or pharmacodynamics, and immune stimulation. Thus, the optimal design of an antisense oligonucleotide according to the invention requires many considerations beyond simple design of a complementary sequence. Thus, preparation of TLR5-targeted antisense oligonucleotides according to the invention is intended to incorporate changes necessary to limit secondary structure interference with antisense activity, enhance the oligonucleotide's target specificity, minimize interaction with binding or competing factors (for example, proteins), optimize cellular uptake, stability, bioavailability, pharmacokinetics and pharmacodynamics, and/or inhibit, prevent or suppress immune cell activation.

It has been determined that the human TLR5 gene is expressed as a 3.3 kb transcript that is expressed most abundant in peripheral blood leukocytes, ovary, and prostate (Chaudhary et al. (1998) Blood 91:4020-4027). The transcript contains a 2.6 kb coding region, which encodes an 858 amino acid protein in humans. The oligonucleotides of the invention were designed to specifically hybridize with optimally available portions of the TLR5 nucleic acid sequence that most effectively act as a target for inhibiting TLR5 expression. These targeted regions of the TLR5 gene include portions of the known exons or 5' untranslated region. In addition, intron-exon boundaries, 3' untranslated regions and introns are potentially useful targets for antisense inhibition of TLR5 expression. The nucleotide sequences of some representative, non-limiting oligonucleotides specific for human TLR5 have SEQ ID NOS: 1-173. The nucleotide sequences of optimized oligonucleotides according to the invention include those having SEQ ID NOS: 6, 40, 66, 78, 118, 140 or 149.

The oligonucleotides of the invention are at least 14 nucleotides in length, but are preferably 15 to 60 nucleotides long, preferably 20 to 50 nucleotides in length. In some embodiments, these oligonucleotides contain from about 14 to 28 nucleotides or from about 16 to 25 nucleotides or from about 18 to 22 nucleotides or 20 nucleotides. These oligonucleotides can be prepared by the art recognized methods such as phosphoramidate or H-phosphonate chemistry which can be carried out manually or by an automated synthesizer. The synthetic TLR5 antisense oligonucleotides of the invention may also be modified in a number of ways without compromising their ability to hybridize to TLR5 mRNA. Such modifications may include at least one internucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate triester, acetamidate or carboxymethyl ester or a combination of these and other internucleotide linkages between the 5' end of one nucleotide and the 3' end of another nucleotide in which the 5' nucleotide phosphodiester linkage has been replaced with any number of chemical groups.

For example, U.S. Pat. No. 5,149,797 describes traditional chimeric oligonucleotides having a phosphorothioate core region interposed between methylphosphonate or phosphoramidate flanking regions. U.S. Pat. No. 5,652,356 discloses "inverted" chimeric oligonucleotides comprising one or more nonionic oligonucleotide region (e.g. alkylphosphonate and/or phosphoramidate and/or phosphotriester internucleoside linkage) flanked by one or more region of oligonucleotide phosphorothioate. Various oligonucleotides with modified internucleotide linkages can be prepared according to standard methods. Phosphorothioate linkages may be mixed Rp and Sp enantiomers, or they may be made stereoregular or substantially stereoregular in either Rp or Sp form according to standard procedures.

Oligonucleotides which are self-stabilized are also considered to be modified oligonucleotides useful in the methods of the invention (Tang et al. (1993) Nucleic Acids Res. 20:2729-2735). These oligonucleotides comprise two regions: a target hybridizing region; and a self-complementary region having an oligonucleotide sequence complementary to a nucleic acid sequence that is within the self-stabilized oligonucleotide.

Other modifications include those which are internal or at the end(s) of the oligonucleotide molecule and include additions to the molecule of the internucleoside phosphate linkages, such as cholesterol, cholesteryl, or diamine compounds with varying numbers of carbon residues between the amino groups and terminal ribose, deoxyribose and phosphate modifications which cleave, or crosslink to the opposite chains or to associated enzymes or other proteins which bind to the genome. Examples of such modified oligonucleotides include oligonucleotides with a modified base and/or sugar such as arabinose instead of ribose, or a 3', 5'-substituted oligonucleotide having a sugar which, at both its 3' and 5' positions, is attached to a chemical group other than a hydroxyl group (at its 3' position) and other than a phosphate group (at its 5' position).

Other examples of modifications to sugars include modifications to the 2' position of the ribose moiety which include but are not limited to 2'-O-substituted with an —O-alkyl group containing 1-6 saturated or unsaturated carbon atoms, or with an —O-aryl, or —O-allyl group having 2-6 carbon atoms wherein such —O-alkyl, —O-aryl or —O-allyl group may be unsubstituted or may be substituted, for example with halo, hydroxy, trifluoromethyl cyano, nitro acyl acyloxy, alkoxy, carboxy, carbalkoxyl or amino groups. None of these substitutions are intended to exclude the native 2'-hydroxyl group in the case of ribose or 2'1-H— in the case of deoxyribose.

The oligonucleotides according to the invention can comprise one or more ribonucleotides. For example, U.S. Pat. No. 5,652,355 discloses traditional hybrid oligonucleotides having regions of 2'-O-substituted ribonucleotides flanking a DNA core region. U.S. Pat. No. 5,652,356 discloses an "inverted" hybrid oligonucleotide which includes an oligonucleotide comprising a 2'-O-substituted (or 2' OH, unsubstituted) RNA region which is in between two oligodeoxyribonucleotide regions, a structure that "inverted relative to the "traditional" hybrid oligonucleotides. Non-limiting examples of particularly useful oligonucleotides of the invention have 2'-O-alkylated ribonucleotides at their 3', 5', or 3' and 5' termini, with at least four or five contiguous nucleotides being so modified. Non-limiting examples of 2'-O-alkylated groups include 2'-O-methyl, 2'-O-ethyl, 2'-O-propyl, 2'-O-butyls and 2'-O-methoxy-ethyl.

Other modified oligonucleotides are capped with a nuclease resistance-conferring bulky substituent at their 3' and/or 5' end(s), or have a substitution in one non-bridging oxygen per nucleotide. Such modifications can be at some or all of the internucleoside linkages, as well as at either or both ends of the oligonucleotide and/or in the interior of the molecule.

The oligonucleotides of the invention can be administered in combination with one or more antisense oligonucleotides or other nucleic acid containing compounds that are not targeted to the same region as the antisense molecule of the invention. Such other nucleic acid containing compounds include, but are not limited to, ribozymes, RNAi molecules, siRNA, miRNA, and aptamers. In addition, the oligonucleotides of the invention can be administered in combination with one or more compound or composition that would activate a TLR5-mediated immune response but for the presence of the TLR5 antisense oligonucleotide according to the invention. In addition, the oligonucleotides of the invention can be administered in combination with one or more vaccines, antigens, antibodies, cytotoxic agents, allergens, antibiotics, TLR antagonists, siRNA, miRNA, antisense oligonucleotides, aptamers, peptides, proteins, gene therapy vectors, DNA vaccines, adjuvants, kinase inhibitors, inhibitors of STAT protein or co-stimulatory molecules or combinations thereof.

A non-limiting list of TLR5 antisense oligonucleotides are shown in SEQ ID NO. 1 through SEQ ID NO. 173 and Table 2 below. Optimized antisense oligonucleotides according to the invention include those having SEQ ID NOS: 6, 40, 66, 78, 118, 140 or 149. In Table 2, the oligonucleotide-based TLR5 antisense compounds have all phosphorothioate (PS) linkages. Those skilled in the art will recognize, however, that phosphodiester (PO) linkages, or a mixture of PS and PO linkages can be used.

TABLE 2

| SEQ ID NO./ AS NO. | Position of Binding | Antisense Sequence Orientation is 5'-3' |
|---|---|---|
| 1 | 1 | CGCTCGGGCTCCTGAAAACC |
| 2 | 21 | GGACGCAAAAGCGGCGCCCT |
| 3 | 41 | CGCCACGGTTGGCTCCTCCC |
| 4 | 61 | ACGCCTCCCCGCCGCCCTG |
| 5 | 81 | CGGCAGAGTGAGACTCTGGG |
| 6 | 103 | GGCAGTGGTTGCAGTCAGGC |
| 7 | 121 | TGCAGTCAGCCGAGATTGTG |
| 8 | 141 | TGAACCCTGGAGGCAGTGGT |
| 9 | 161 | GCTGAGGCAAGAGAATCGCT |
| 10 | 181 | TAATCCCAGCTACTTGGGAG |
| 11 | 201 | GGAACATGAACATCAATCTG |
| 12 | 221 | TGAATCTTGTAGTAGTGTCA |
| 13 | 241 | TGTCAGTAGCATCAGGAGTA |
| 14 | 261 | TGACTGTGGAGAAGCCACGT |
| 15 | 281 | GTATAGCATCCCTGGTTTGG |
| 16 | 301 | GATGAGAGTAGGGAAGTCCA |
| 17 | 321 | AAGGTCAGGGGCTGGAGCA |
| 18 | 341 | CAGGAAAGCTGGGCAACTAT |
| 19 | 361 | TGATGGGCAAAGTCAATTGC |
| 20 | 381 | GGATGCTAAATCCTGTGTAT |
| 21 | 401 | GAGGCTCCGACATCTTCCCT |
| 22 | 421 | CAATTAGAAAATTAACATCT |
| 23 | 441 | TCGGACAGCGCCAACATTCT |
| 24 | 461 | TTGTTTTCCTGTCTCCAGGT |
| 25 | 481 | GAATCAGGAGAAAGGACTTT |
| 26 | 501 | TCAGTATTTATTTTTTGGT |
| 27 | 521 | TCTCATCACAGTGATGGTAG |
| 28 | 541 | AGTTCCTGAGACTATAGGAA |
| 29 | 561 | CCTGGTTGTTTAAAGACTTC |
| 30 | 581 | TATTCTAGGGGCAGAGGGTC |
| 31 | 601 | AGGGACTTCTAGTATGTTCT |
| 32 | 621 | ATCCTCGTTGTCCTAGCAGA |
| 33 | 641 | GGTCCAGGTGGTCTCCCATG |
| 34 | 661 | GAGCACCACTCCTAGGAGAA |

TABLE 2-continued

| SEQ ID NO./ AS NO. | Position of Binding | Antisense Sequence Orientation is 5'-3' |
|---|---|---|
| 35 | 681 | CCAAACACAGGACCGGCCAT |
| 36 | 701 | CAAAGGAGCAGGAAGGAATT |
| 37 | 721 | ATAAAAGGCTATTCGGCCAT |
| 38 | 741 | TGGGTGAGGTTGCAGAAACG |
| 39 | 761 | TGTTGAGGACCTGGGGGACC |
| 40 | 771 | CUCUCAGTGGTGTTGAGGAC |
| 41 | 781 | CAGCAGGAGCCTCTCAGTGG |
| 42 | 801 | GTCCTGATATAGTTGAAGCT |
| 43 | 821 | GGAAGGATGAAGCAGTGACT |
| 44 | 841 | CTGCAGCTGTTCCAGAAAGG |
| 45 | 861 | TGGCTCCCGAGCTCCAGCAG |
| 46 | 881 | CAATAGTCAAGGGGGTATAC |
| 47 | 901 | GTTTCTGAAGGCCTCCTTGT |
| 48 | 921 | AAGATTCTAAGGTTGGGCAG |
| 49 | 941 | TCTTACTACTTCCCAGGTCC |
| 50 | 961 | ATCTGGATGCAAGAAGTATA |
| 51 | 981 | TGGAACAGTCCCTGAAAAGC |
| 52 | 1001 | ACAGTCTAAGTTCAAACAGA |
| 53 | 1021 | ATCAGAGAGACCACAGAAAT |
| 54 | 1041 | TAACCATCTTTCAATACAGC |
| 55 | 1061 | AAGCCTTTAAATTTCTGAAA |
| 56 | 1081 | GGATAGATCCAAGCGAGTTA |
| 57 | 1101 | AGGCTACGAATCTGATTTTT |
| 58 | 1121 | CAAATGAAGGATGAAGGTAA |
| 59 | 1141 | CTTTAAGGAATTCAACTTCC |
| 60 | 1161 | TTGGAGGAAAAATCTATGGA |
| 61 | 1181 | CACATACAAGGAATATTTGG |
| 62 | 1201 | TAGGGGCTCGAGCTCATGTT |
| 63 | 1221 | AAGGAGAGCGTTTTCCCTTG |
| 64 | 1241 | TATTAGCTGCGAGGCTAAAA |
| 65 | 1261 | TGAGACTCTGCTATACAAGC |
| 66 | 1270 | CCAGTCCACTGAGACTCUGC |
| 67 | 1281 | ATACATTTTCCCCAGTCCAC |
| 68 | 1301 | CCATGTTTCTGAATGGGTTC |
| 69 | 1321 | AACATCTAGTATCTCCAGCA |
| 70 | 1341 | ACTGTCCAGCCATTTCCAGA |
| 71 | 1361 | TAAAGTTTCCTGTGATGTCC |
| 72 | 1381 | GCTTTTGCTGATGGCATTGC |

TABLE 2-continued

| SEQ ID NO./ AS NO. | Position of Binding | Antisense Sequence Orientation is 5'-3' |
|---|---|---|
| 73 | 1401 | AGAATCAAAGAGAAGGCCTG |
| 74 | 1421 | CACCCATGATGTGGTGGGCA |
| 75 | 1441 | GTTATGGAAGCCAAACCCGG |
| 76 | 1461 | TTCTGGTCAGGATCTTTGAT |
| 77 | 1481 | TGGCCAGGCCAGCAAATGTG |
| 78 | 1504 | AUCCAGGTGTCTCACTGAAC |
| 79 | 1521 | ACAAACCCATGTGAAAGATC |
| 80 | 1541 | CTCGTGAGTTCAGGGAGAAG |
| 81 | 1561 | ATCCTTGAGTGTCTCAAAGA |
| 82 | 1581 | GCAAGGTTCAGAACCTTCAA |
| 83 | 1601 | TCTTATTTATCTTGTTGTAG |
| 84 | 1621 | GTAAAATGCTTCATCTGCAA |
| 85 | 1641 | ACTTGGAGGTTGTCAAGTCC |
| 86 | 1661 | GGTTATATGACAAATTGAGA |
| 87 | 1681 | ACTGTAAAGTTCCCCCAGAA |
| 88 | 1701 | GGTAGTCCATAGAAATTCGA |
| 89 | 1721 | AATCAATGTAGGCTACCTTA |
| 90 | 1741 | TGCAATGTGATTCTTTTGCA |
| 91 | 1761 | AATGTTTGGTCTTGAATTAT |
| 92 | 1781 | GTAATTTTTCCAGGAATTTG |
| 93 | 1801 | GTCTCGGAGATCCAAGGTCT |
| 94 | 1821 | TGAATGGTTGTAAGAGCATT |
| 95 | 1841 | CGGGTATGCTTGGAATAAAA |
| 96 | 1861 | ATTGCCACTCAAGAAGATAT |
| 97 | 1881 | TTTGGCAAAGTCACTAGTTT |
| 98 | 1901 | GGTTCGCTGTAAGGTTGATC |
| 99 | 1921 | GTTTTCTGATAAGTGGATGA |
| 100 | 1941 | ATATCTAGATTTTCTAGCCT |
| 101 | 1961 | CCCGTAGGAGAAAGTAGAGA |
| 102 | 1981 | GAGAATCTGGAGATGAGGTA |
| 103 | 2001 | AAGCGATTTTGATTTAAAAT |
| 104 | 2021 | GATCTCCACTACAGGAGGAG |
| 105 | 2041 | GGGATTCTCTGAAGGGGTTT |
| 106 | 2061 | AGGAAAAGCTGTTCTAAGCT |
| 107 | 2081 | GTTGCAACATATTTTCTCCA |
| 108 | 2101 | GAGCTCAGTTTCCCAGGCAA |
| 109 | 2121 | CCCTCAAAAACATCCCAACA |
| 110 | 2141 | GAACTTGAAGATGAGAAAGT |
| 111 | 2161 | ATAGTTATGATTCAAATACA |
| 112 | 2181 | CCTGGTGGAAGGGAATTAAG |
| 113 | 2201 | CAGTCAGATGGCTAAATACT |
| 114 | 2221 | GAGGCTTAGTCCCCTTAATG |
| 115 | 2241 | ACTGTCAGCCTGTTGGAGTT |
| 116 | 2261 | GTAAATCATTGTGAGAAAGA |
| 117 | 2281 | CAGGATCTCTAAATTAGCAG |
| 118 | 2300 | GCUGGTTCCTGGATATGUCC |
| 119 | 2321 | CATCAGGATTAGGAGCTAGG |
| 120 | 2341 | GACACTAAGTGATACAAATA |
| 121 | 2361 | TTGTTATGAGTTATATCCAA |
| 122 | 2381 | GTTCACATTCACAAATGAAC |
| 123 | 2401 | CCAATTGATAAAAGTGCTAA |
| 124 | 2421 | GTGACATTGGTGTGATTAAG |
| 125 | 2441 | CTGCAGGAGGCCCAGCTATA |
| 126 | 2461 | AGGGTACACACAATATATGT |
| 127 | 2481 | GAAACCCCAGAGAACGAGTC |
| 128 | 2501 | CCGTGGAAAGAGAGAAGAGG |
| 129 | 2521 | TTCCTCTTCATCACAACCTT |
| 130 | 2541 | AACTTTAGGGACTTTAAGAC |
| 131 | 2561 | TGCATACAATGAAAAGGGAG |
| 132 | 2581 | GAACAGAGTCAGAGTGACAG |
| 133 | 2601 | ACTGTGAGGATGGTCATGAG |
| 134 | 2621 | AGAAGCCCCGGAACTTTGTG |
| 135 | 2641 | TGTCTTATAACAGATAAAAC |
| 136 | 2661 | TTGAACACCAGTCTCTGGGC |
| 137 | 2681 | CTGTGCCCTGGGGATGGTCC |
| 138 | 2701 | ATATTTGTACATATCAGGTT |
| 139 | 2721 | CTGAAGCACAAATAGGCATC |
| 140 | 2734 | GAAGTCTTTGCTGCTGAAGC |
| 141 | 2761 | TTTGAGCAAAGCATTCTGCA |
| 142 | 2781 | CTGTATTGAGTGTCCAGGTG |
| 143 | 2801 | GGTTGAATCTGTTTTGGTCA |
| 144 | 2821 | GTCTCTTTCTTCAAAGCACA |
| 145 | 2841 | CGGTTTTCTCCTGGGACAAA |
| 146 | 2861 | CATCCTGGATATTGGCAATG |
| 147 | 2881 | CTTTCTACTGTTCCAGATGG |
| 148 | 2901 | CTGCTCACAAGACAAACGAT |
| 149 | 2915 | CUCUAAGGAAGTGTCTGCUC |

TABLE 2-continued

| SEQ ID NO./ AS NO. | Position of Binding | Antisense Sequence Orientation is 5'-3' |
|---|---|---|
| 150 | 2941 | ACTGAAGGCTTCAAGGCACC |
| 151 | 2961 | AAGCACCTGCCCTGGGCATA |
| 152 | 2981 | GAGCACTGTTAAGGTCAGAT |
| 153 | 3001 | CCCAACCACCACCATGATGA |
| 154 | 3021 | AACTGGTACTGGGACAAGGA |
| 155 | 3041 | TGATGGATTGATGTTTCATC |
| 156 | 3061 | CTGTTTCTGTACAAAGCCTC |
| 157 | 3081 | TCAGGCCACCTCAAATACTG |
| 158 | 3101 | AGCCAACATCCTGGAGATCC |
| 159 | 3121 | AGAGAGTTTATGAAGAAACC |
| 160 | 3141 | TCTTTCTTTAGTATCTGTTG |
| 161 | 3161 | TGTCTTTCTTCTTTTCTTTT |
| 162 | 3181 | AGTTTGCAACGGAATGTTAT |
| 163 | 3201 | GATTAGGAGATGGTTGCTAC |
| 164 | 3221 | AAGTTGGAAATTGCTCCTTT |
| 165 | 3241 | AGTTATTTGTGGCTTGAGAT |
| 166 | 3261 | GGTGCAAATACAAAGTGAAG |
| 167 | 3281 | GGACCCCAAAATGATAACTT |
| 168 | 3301 | AAAAAAAAAACCTCCAGAGA |
| 169 | 3321 | GTTTTCATAGTAGCAAAAAG |
| 170 | 3341 | AAAATTGAGAGATTTATGTT |
| 171 | 3361 | CAGAACATGGTGTTGATACG |
| 172 | 3381 | CCATTTGGAGGTTAGTGAGA |
| 173 | 3401 | TTTTCTAGATCTATTATTTT |

AS is an abbreviation for antisense. Underlined nucleotides are 2'-O-methylribonucleotides; all others are 2'-deoxyribonucleotides. In the exemplary antisense oligonucleotides according to the invention, when a "CG" dinucleotide is contained in the sequence, such oligonucleotide is modified to remove or prevent the immune stimulatory properties of the oligonucleotide.

In another aspect, the invention provides a composition comprising at least one optimized antisense oligonucleotide according to the invention and a physiologically acceptable carrier, diluent or excipient. The characteristics of the carrier will depend on the route of administration. Such a composition may contain, in addition to the synthetic oligonucleotide and carrier, diluents, fillers, salts, buffers, stabilizers, solubilizers, and other materials well known in the art. The pharmaceutical composition of the invention may also contain other active factors and/or agents which enhance inhibition of TLR5 expression. For example, combinations of synthetic oligonucleotides, each of which is directed to different regions of the TLR5 mRNA, may be used in the pharmaceutical compositions of the invention. The pharmaceutical composition of the-invention may further contain nucleotide analogs such as azidothymidine, dideoxycytidine, dideoxyinosine, and the like. Such additional factors and/or agents may be included in the pharmaceutical composition to produce a synergistic, additive or enhanced effect with the synthetic oligonucleotide of the invention, or to minimize side-effects caused by the synthetic oligonucleotide of the invention. The pharmaceutical composition of the invention may be in the form of a liposome in which the synthetic oligonucleotides of the invention is combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. One particularly useful lipid carrier is lipofectin. Preparation of such liposomal formulations is within the level of skill in the art, as disclosed, for example, in U.S. Pat. Nos. 4,235,871; 4,501,728; 4,837,028; and 4,737,323. The pharmaceutical composition of the invention may further include compounds such as cyclodextrins and the like that enhance delivery of oligonucleotides into cells or slow release polymers.

In another aspect, the invention provides a method of inhibiting TLR5 expression. In this method, an oligonucleotide or multiple oligonucleotides of the invention are specifically contacted or hybridized with TLR5 mRNA either in vitro or in a cell.

In another aspect, the invention provides methods for inhibiting the expression of TLR5 in a mammal, particularly a human, such methods comprising administering to the mammal a compound or composition according to the invention. One skilled in the art would recognize that the antisense compounds and compositions according to the invention can be administered through a variety of means. Once such means for administration is according to Example 3. The antisense activity of a compound or composition according to the invention can be determined by measuring TLR5 mRNA and TLR5 protein concentration. The data is anticipated to demonstrate that administration of an exemplary TLR5 antisense oligonucleotide according to the invention can cause down-regulation of TLR5 expression in vivo.

In another aspect, the invention provides a method for inhibiting a TLR-mediated immune response in a mammal, the method comprising administering to the mammal a TLR5 antisense oligonucleotide according to the invention in a pharmaceutically effective amount, wherein routes of administration include, but are not limited to, parenteral, intramuscular, subcutaneous, intraperitoneal, intraveneous, mucosal delivery, oral, sublingual, transdermal, topical, inhalation, intranasal, aerosol, intraocular, intratracheal, intrarectal, vaginal, by gene gun, dermal patch or in eye drop or mouthwash form. One skilled in the art would recognize that one such administration can be accomplished according to Example 3, or by known methods. The antisense activity of compound or composition according to the invention can be determined by measuring biomarkers related to TLR5 signaling, for example, but not limited to, measuring IL-12. The data is anticipated to demonstrate that administration of an exemplary TLR5 antisense oligonucleotide according to the invention can cause down-regulation of TLR5 expression in vivo and prevent the induction of IL-12 by a TLR5 agonist. More generally, the data is anticipated to demonstrate the ability of a TLR5 antisense oligonucleotide according to the invention to inhibit the induction of pro-inflammatory cytokines by a TLR5 agonist.

In another aspect, the invention provides a method for therapeutically treating a mammal having a disease mediated by TLR5, such method comprising administering to the mammal, particularly a human, a TLR5 antisense oligonucleotide of the invention in a pharmaceutically effective amount.

In certain embodiments, the disease is cancer, an autoimmune disorder, airway inflammation, inflammatory disorders, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma or a disease caused by a pathogen. Preferred autoimmune disorders include without limitation lupus erythematosus, multiple sclerosis, type I diabetes mellitus, irritable bowel syndrome, Chron's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis ("giant cell arteritis"), vasculitis, vitiligo, vulvodynia and Wegener's granulomatosis. In certain embodiments, inflammatory disorders include without limitation airway inflammation, asthma, autoimmune diseases, chronic inflammation, chronic prostatitis, glomerulonephritis, Behçet's disease, hypersensitivities, inflammatory bowel disease, reperfusion injury, rheumatoid arthritis, transplant rejection, ulcerative colitis, uveitis, conjunctivitis and vasculitis.

In another aspect, the invention provides methods for preventing a disease or disorder in a mammal, particularly a human, at risk of contracting or developing a disease or disorder mediated by TLR5. Such method comprises administering to the mammal a prophylactically effective amount of an antisense oligonucleotide or composition according to the invention. Such diseases and disorders include, without limitation, cancer, an autoimmune disorder, airway inflammation, inflammatory disorders, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma or a disease caused by a pathogen in a vertebrate. Autoimmune disorders include, without limitation, lupus erythematosus, multiple sclerosis, type I diabetes mellitus, irritable bowel syndrome, Chron's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis ("giant cell arteritis"), vasculitis, vitiligo, vulvodynia and Wegener's granulomatosis. Inflammatory disorders include, without limitation, airway inflammation, asthma, autoimmune diseases, chronic inflammation, chronic prostatitis, glomerulonephritis, Behçet's disease, hypersensitivities, inflammatory bowel disease, reperfusion injury, rheumatoid arthritis, transplant rejection, ulcerative colitis, uveitis, conjunctivitis and vasculitis.

In another aspect, the invention provides a method for inhibiting TLR5 expression and activity in a mammal, comprising administering to the mammal an antisense oligonucleotide complementary to TLR5 mRNA and an antagonist of TLR5 protein, a kinase inhibitor or an inhibitor of STAT protein. Accordingly, TLR5 expression is inhibited by the antisense oligonucleotide, while any TLR5 protein residually expressed is inhibited by the antagonist. Preferred antagonists include anti-TLR5 antibodies or binding fragments or peptidomimetics thereof, RNA-based compounds, oligonucleotide-based compounds, and small molecule inhibitors of TLR5 activity or TLR5 signaling.

In the various methods according to the invention, a therapeutically or prophylactically effective amount of a synthetic oligonucleotide of the invention and effective in inhibiting the expression of TLR5 is administered to a cell. This cell may be part of a cell culture, a neovascularized tissue culture, or may be part or the whole body of a mammal such as a human or other mammal. Administration of the therapeutic compositions of TLR5 antisense oligonucleotide can be carried out using known procedures at dosages and for periods of time effective to reduce symptoms or surrogate markers of the disease, depending on the condition and response, as determined by those with skill in the art. It may be desirable to administer simultaneously, or sequentially a therapeutically effective amount of one or more of the therapeutic TLR5 antisense oligonucleotides of the invention to an individual as a single treatment episode. In some exemplary embodiments of the methods of the invention described above, the oligonucleotide is administered locally and/or systemically. The term "administered locally" refers to delivery to a defined area or region of the body, while the term "systemic administration" is meant to encompass delivery to the whole organism.

In any of the methods according to the invention, one or more of the TLR5 antisense oligonucleotide can be administered alone or in combination with any other agent useful for treating the disease or condition that does not diminish the immune modulatory effect of the TLR5 antisense oligonucleotide. In any of the methods according to the invention, the agent useful for treating the disease or condition includes, but is not limited to, one or more vaccines, antigens, antibodies, cytotoxic agents, allergens, antibiotics, antisense oligonucleotides, TLR agonist, TLR antagonist, siRNA, miRNA, aptamers, peptides, proteins, gene therapy vectors, DNA vaccines, adjuvants or kinase inhibitors to enhance the specificity or magnitude of the immune response, or co-stimulatory molecules such as cytokines, chemokines, protein ligands, transactivating factors, peptides and peptides comprising modified amino acids. For example, in the treatment of autoimmune disease, it is contemplated that the TLR5 antisense oligonucleotide may be administered in combination with one or more targeted therapeutic agents and/or monoclonal antibodies. Alternatively, the agent can include DNA vectors encoding for antigen or allergen. In these embodiments, the TLR5 antisense oligonucleotide of the invention can produce direct immune modulatory or suppressive effects. When co-administered with one or more other therapies, the synthetic oligonucleotide of the invention may be administered either simultaneously with the other treatment(s), or sequentially.

In the various methods according to the invention the route of administration may be, without limitation, parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form.

When a therapeutically effective amount of synthetic oligonucleotide of the invention is administered orally, the synthetic oligonucleotide will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% synthetic oligonucleotide and preferably from about 25 to 90% synthetic oligonucleotide. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution or glycols such as ethylene glycol, propylene glycol or polyethylene glycol. When administered in liquid form, the pharmaceutical composition contains from about 0.5 to 90% by weight of the synthetic oligonucleotide or from about 1 to 50% synthetic oligonucleotide.

When a therapeutically effective amount of synthetic oligonucleotide of the invention is administered by parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form, the synthetic antisense oligonucleotide will be in the form of a pyrogen-free, parenterally acceptable aqueous solution. The preparation of such parenterally acceptable solutions, having due regard to pH, isotonicity, stability, and the like, is within the skill in the art. A pharmaceutical composition for parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form should contain, in addition to the synthetic oligonucleotide, an isotonic vehicle such as Sodium Chloride Injection, Ringer's Injection, Dextrose Injection, Dextrose and Sodium Chloride Injection, Lactated Ringer's Injection or other vehicle as known in the art. The pharmaceutical composition of the present invention may also contain stabilizers, preservatives, buffers, antioxidants or other additives known to those of skill in the art.

When administered parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form, doses ranging from 0.01% to 10% (weight/volume) may be used. When administered in liquid form, a liquid carrier such as water, petroleum, oils of animal or plant origin such as peanut oil, mineral oil, soybean oil, sesame oil or synthetic oils may be added. Topical administration may be by liposome or transdermal time-release patch.

The amount of synthetic oligonucleotide in the pharmaceutical composition of the present invention will depend upon the nature and severity of the condition being treated, and on the nature of prior treatments which the patient has undergone. It is contemplated that the various pharmaceutical compositions used to practice the method of the present invention should contain about 10 micrograms to about 20 mg of synthetic oligonucleotide per kg body or organ weight.

The duration of intravenous therapy using the pharmaceutical composition of the present invention will vary, depending on the severity of the disease being treated and the condition and potential idiosyncratic response of each individual patient.

Some diseases lend themselves to acute treatment while others require longer term therapy. Both acute and long term intervention in diseases are worthy goals. Injections of antisense oligonucleotides against TLR5 can be an effective means of inhibiting certain diseases in an acute situation. However for long term therapy over a period of weeks, months or years, systemic delivery (intraperitoneal, intramuscular, subcutaneous, intravenous) either with carriers such as saline, slow release polymers or liposomes are likely to be considered.

In some chronic diseases, systemic administration of oligonucleotides may be preferable. The frequency of injections is from continuous infusion to once a month, several times per month or less frequently will be determined based on the disease process and the biological half life of the oligonucleotides.

The oligonucleotides and methods of the invention are also useful for examining the function of the TLR5 gene in a cell or in a control mammal or in a mammal afflicted with a disease associated with TLR5 or immune stimulation through TLR5. In such use, the cell or mammal is administered the oligonucleotide, and the expression of TLR5 mRNA or protein is examined.

Without intending to be limited to any theory or mechanism, it is generally believed that the activity of oligonucleotides according to the invention depends on the hybridization of the oligonucleotide to the target nucleic acid (e.g. to at least a portion of a genomic region, gene or mRNA transcript thereof), thus disrupting the function of the target. Such hybridization under physiological conditions is measured as a practical matter by observing interference with the function of the nucleic acid sequence. Thus, an exemplary oligonucleotide used in accordance with the invention is capable of forming a stable duplex (or triplex in the Hoogsteen or other hydrogen bond pairing mechanism) with the target nucleic acid; activating RNase H or other in vivo enzymes thereby causing effective destruction of the target RNA molecule; and is capable of resisting nucleolytic degradation (e.g. endonuclease and exonuclease activity) in vivo. A number of the modifications to oligonucleotides described above and others which are known in the art specifically and successfully address each of these exemplary characteristics.

The patents and publications cited herein reflect the level of knowledge in the art and are hereby incorporated by reference in their entirety. Any conflict between the teachings of these patents and publications and this specification shall be resolved in favor of the latter. Those skilled in the art will recognize, or be able to ascertain, using no more than routine experimentation, numerous equivalents to the specific substances and procedures described herein. For example, antisense oligonucleotides that overlap with the oligonucleotides may be used. Such equivalents are considered to be within the scope of this invention.

The following examples illustrate the exemplary modes of making and practicing the present invention, but are not meant to limit the scope of the invention since alternative methods may be utilized to obtain similar results.

EXAMPLES

Example 1

Preparation of TLR5-Specific Antisense Oligonucleotides

Chemical entities according to the invention were synthesized on a 1 μmol to 0.1 mM scale using an automated DNA synthesizer (OligoPilot II, AKTA, (Amersham) and/or Expedite 8909 (Applied Biosystem)), following the linear synthesis procedure outlined in FIG. 1.

5'-DMT dA, dG, dC and T phosphoramidites were purchased from Proligo (Boulder, Colo.). 5'-DMT 7-deaza-dG and araG phosphoramidites were obtained from Chemgenes (Wilmington, Mass.). DiDMT-glycerol linker solid support was obtained from Chemgenes. 1-(2'-deoxy-β-D-ribofuranosyl)-2-oxo-7-deaza-8-methyl-purine amidite was obtained from Glen Research (Sterling, Va.), 2'-O-methylribonucleoside amidites were obtained from Promega (Obispo, Calif.). All compounds according to the invention were phosphorothioate backbone modified.

All nucleoside phosphoramidites were characterized by $^{31}$P and $^{1}$H NMR spectra. Modified nucleosides were incorporated at specific sites using normal coupling cycles recommended by the supplier. After synthesis, compounds were deprotected using concentrated ammonium hydroxide and purified by reverse phase HPLC, detritylation, followed by dialysis. Purified compounds as sodium salt form were lyophilized prior to use. Purity was tested by CGE and MALDI-TOF MS. Endotoxin levels were determined by LAL test and were below 1.0 EU/mg.

Example 2

Cell Culture Conditions and Reagents
HEK293 Cell Culture Assays for TLR5 Antisense Activity HEK293 cells stably expressing human TLR5 (Invivogen, San Diego, Calif.) were plated in 48-well plates in 250 μL/well DMEM supplemented with 10% heat-inactivated FBS in a 5% CO2 incubator. At 80% confluence, cultures were transiently transfected with 400 ng/mL of the secreted form of human embryonic alkaline phosphatase (SEAP) reporter plasmid (pNifty2-Seap) (Invivogen) in the presence of 4 μL/mL of lipofectamine (Invitrogen, Carlsbad, Calif.) in culture medium. The SEAP reporter plasmid is inducible by NF-κB. Plasmid DNA and lipofectamine were diluted separately in serum-free medium and incubated at room temperature for 5 min. After incubation, the diluted DNA and lipofectamine were mixed and the mixtures were incubated further at room temperature for 20 min. Aliquots of 25 μL of the DNA/lipofectamine mixture containing 100 ng of plasmid DNA and 1 μL of lipofectamine were added to each well of the cell culture plate, and the cells were transfected for 6 h. After transfection, medium was replaced with fresh culture medium (no antibiotics), antisense compounds were added to the wells, and incubation continued for 18-20 h. Cells were then stimulated with the human TLR5 agonist, Flagellin, at 1.25 μg/ml for 6 h.

At the end of the treatment, 20 μL of culture supernatant was taken from each well and assayed for SEAP assay by the Quanti Blue method according to the manufacturer's protocol (Invivogen). The data are depicted in FIG. 2. The date in FIG. 2 depict NF-κB activity compared to control and demonstrates (i) that exemplary human TLR5 antisense oligonucleotides according to the invention are not immunostimulatory (Antisense Alone); and (ii) that exemplary human TLR5 antisense oligonucleotides according to the invention inhibit TLR5 expression and activation (Agonist Plus AS).

Example 3

In Vivo Activity of TLR5 Antisense Oligonucleotide

Female C57BL/6 mice of 5-6 weeks age (N=3/group) are injected with exemplary murine TLR5 antisense oligonucleotides according to the invention at 5 mg/kg, or PBS, subcutaneously once a day for three days. Subsequent to administration of the TLR5 antisense oligonucleotide, mice are injected with 0.25 mg/kg of a TLR5 agonist subcutaneously. Two hours after administration of the TLR5 agonist, blood is collected and TLR5 mRNA, TLR5 protein, and IL-12 concentrations are determined by ELISA.

What is claimed is:

1. A synthetic antisense oligonucleotide complementary to TLR5 mRNA (SEQ ID NO: 174), wherein the antisense oligonucleotide has a sequence consisting of SEQ ID NOs: 6, 40, 66, 78, 118, 140 or 149, and wherein the oligonucleotide specifically hybridizes to and inhibits the expression of human TLR5.

2. A composition comprising a synthetic antisense oligonucleotide according to claim 1 and a physiologically acceptable carrier.

3. A method for inhibiting the expression of TLR5, the method comprising administering a synthetic antisense oligonucleotide according to claim 1.

4. A method for inhibiting the expression of TLR5, the method comprising administering a composition according to claim 2.

5. A method for inhibiting the expression of TLR5 in an mammal, the method comprising administering to the mammal a synthetic antisense oligonucleotide according to claim 1.

6. A method for inhibiting the expression of TLR5 in mammal, the method comprising administering to the mammal a composition according to claim 2.

7. A method for down-regulating TLR5 expression and thus preventing undesired TLR5-mediated immune stimulation by a compound that activates TLR5, the method comprising administering a synthetic antisense oligonucleotide according to claim 1 in combination with one or more compounds that would activate a TLR5-mediated immune response but for the presence the antisense oligonucleotide.

8. A method for down-regulating TLR5 expression and thus preventing undesired TLR5-mediated immune stimulation by a compound that activates TLR5, the method comprising administering a composition according to claim 2 in combination with one or more compounds that would activate a TLR5-mediated immune response but for the presence of the composition.

9. The method according to claim 5, wherein the mammal is a human.

10. The method according to claim 3, wherein the route of administration is selected from the group consisting of parenteral, intramuscular, subcutaneous, intraperitoneal, intraveneous, mucosal delivery, oral, sublingual, transdermal, topical, inhalation, intranasal, aerosol, intraocular, intratracheal, intrarectal, vaginal, gene gun, dermal patch, eye drop and mouthwash.

11. The method according to claim 3, comprising further administering one or more vaccines, antigens, antibodies, cytotoxic agents, allergens, antibiotics, antisense oligonucleotides, TLR agonist, TLR antagonist, siRNA, miRNA, antisense oligonucleotides, aptamers, proteins, gene therapy vectors, DNA vaccines, adjuvants, co-stimulatory molecules or combinations thereof.

12. A method for inhibiting TLR5 expression and activity in a mammal, comprising administering to the mammal an antisense oligonucleotide according to claim 1 and an antagonist of TLR5 protein.

13. The method according to claim 12, wherein the TLR5 antagonist is selected from the group consisting of anti-TLR5 antibodies or binding fragments or peptidomimetics thereof, RNA-based compounds, oligonucleotide-based compounds, and small molecule inhibitors of TLR5 activity.

14. The synthetic antisense oligonucleotide according to claim 1, wherein the antisense oligonucleotide has a sequence consisting of SEQ ID NO: 6.

15. The synthetic antisense oligonucleotide according to claim 1, wherein the antisense oligonucleotide has a sequence consisting of SEQ ID NO: 40.

16. The synthetic antisense oligonucleotide according to claim 1, wherein the antisense oligonucleotide has a sequence consisting of SEQ ID NO: 66.

17. The synthetic antisense oligonucleotide according to claim 1, wherein the antisense oligonucleotide has a sequence consisting of SEQ ID NO: 78.

18. The synthetic antisense oligonucleotide according to claim 1, wherein the antisense oligonucleotide has a sequence consisting of SEQ ID NO: 118.

19. The synthetic antisense oligonucleotide according to claim 1, wherein the antisense oligonucleotide has a sequence consisting of SEQ ID NO: 140.

20. The synthetic antisense oligonucleotide according to claim 1, wherein the antisense oligonucleotide has a sequence consisting of SEQ ID NO: 149.

21. A combination comprising the synthetic antisense oligonucleotide according to claim 1 and a TLR5 antagonist.

22. A combination comprising the synthetic antisense oligonucleotide according to claim 1 and a kinase inhibitor.

23. A combination comprising the synthetic antisense oligonucleotide according to claim 1 and an inhibitor of STAT protein.

\* \* \* \* \*

SEQUENCE LISTING

<160> NUMBER OF SEQ ID NOS: 174

<210> SEQ ID NO 1
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 1
cgctcgggct cctgaaaacc          20

<210> SEQ ID NO 2
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 2
ggacgcaaaa gcggcgccct          20

<210> SEQ ID NO 3
<211> LENGTH: 20
<212> TYPE: DNA
<213> ORGANISM: Artificial Sequence
<220> FEATURE:

```
<223> OTHER INFORMATION: Antisense oligonucleotide

<400> SEQUENCE: 3
cgccacggtt ggctcctccc                                              20

<210> SEQ ID NO 4
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 4
acgcctcccc gcgccgcctg                                              20

<210> SEQ ID NO 5
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 5
cggcagagtg agactctggg                                              20

<210> SEQ ID NO 6
<211> LENGTH: 20
<212> TYPE: DNA
<213> ORGANISM: Artificial Sequence
<220> FEATURE:
<223> OTHER INFORMATION: Antisense oligonucleotide
<220> FEATURE:
<221> NAME/KEY: misc_feature
<222> LOCATION: (1)..(4)
<223> OTHER INFORMATION: 2'-O-methylribonucleotides
<220> FEATURE:
<221> NAME/KEY: misc_feature
<222> LOCATION: (17)..(20)
<223> OTHER INFORMATION: 2'-O-methylribonucleotides

<400> SEQUENCE: 6
ggcagtggtt gcagtcaggc                                              20

<210> SEQ ID NO 7
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 7
tgcagtcagc cgagattgtg                                              20

<210> SEQ ID NO 8
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 8
tgaaccctgg aggcagtggt                                              20

<210> SEQ ID NO 9
<211> LENGTH: 20
<212> TYPE: DNA
<213> ORGANISM: Artificial Sequence
<220> FEATURE:
```

-continued

<223> OTHER INFORMATION: Antisense oligonucleotide

<400> SEQUENCE: 9
gctgaggcaa gagaatcgct                                           20

<210> SEQ ID NO 10
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 10
taatcccagc tacttgggag                                           20

<210> SEQ ID NO 11
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 11
ggaacatgaa catcaatctg                                           20

<210> SEQ ID NO 12
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 12
tgaatcttgt agtagtgtca                                           20

<210> SEQ ID NO 13
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 13
tgtcagtagc atcaggagta                                           20

<210> SEQ ID NO 14
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 14
tgactgtgga gaagccacgt                                           20

<210> SEQ ID NO 15
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 15
gtatagcatc cctggtttgg                                           20

<210> SEQ ID NO 16

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 16
gatgagagta gggaagtcca                                                20

<210> SEQ ID NO 17
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 17
aaggtcaggg ggctggagca                                                20

<210> SEQ ID NO 18
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 18
caggaaagct gggcaactat                                                20

<210> SEQ ID NO 19
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 19
tgatgggcaa agtcaattgc                                                20

<210> SEQ ID NO 20
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 20
ggatgctaaa tcctgtgtat                                                20

<210> SEQ ID NO 21
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 21
gaggctccga catcttccct                                                20

<210> SEQ ID NO 22
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 22
```
caattagaaa attaacatct                                           20

<210> SEQ ID NO 23
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 23
tcggacagcg ccaacattct                                           20

<210> SEQ ID NO 24
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 24
ttgttttcct gtctccaggt                                           20

<210> SEQ ID NO 25
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 25
gaatcaggag aaaggacttt                                           20

<210> SEQ ID NO 26
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 26
tcagtatttt attttttggt                                           20

<210> SEQ ID NO 27
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 27
tctcatcaca gtgatggtag                                           20

<210> SEQ ID NO 28
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 28
agttcctgag actataggaa                                           20

<210> SEQ ID NO 29
<211> LENGTH: 20
<212> TYPE: DNA
<213> ORGANISM: Artificial Sequence
<220> FEATURE:

<223> OTHER INFORMATION: Antisense oligonucleotide

<400> SEQUENCE: 29
cctggttgtt taaagacttc                                               20

<210> SEQ ID NO 30
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 30
tattctaggg gcagagggtc                                               20

<210> SEQ ID NO 31
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 31
agggacttct agtatgttct                                               20

<210> SEQ ID NO 32
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 32
atcctcgttg tcctagcaga                                               20

<210> SEQ ID NO 33
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 33
ggtccaggtg gtctcccatg                                               20

<210> SEQ ID NO 34
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 34
gagcaccact cctaggagaa                                               20

<210> SEQ ID NO 35
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 35
ccaaacacag gaccggccat                                               20

<210> SEQ ID NO 36

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 36
caaaggagca ggaaggaatt                                                  20

<210> SEQ ID NO 37
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 37
ataaaaggct attcggccat                                                  20

<210> SEQ ID NO 38
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 38
tgggtgaggt tgcagaaacg                                                  20

<210> SEQ ID NO 39
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 39
tgttgaggac ctgggggacc                                                  20

<210> SEQ ID NO 40
<211> LENGTH: 20
<212> TYPE: DNA
<213> ORGANISM: Artificial Sequence
<220> FEATURE:
<223> OTHER INFORMATION: Antisense oligonucleotide
<220> FEATURE:
<221> NAME/KEY: misc_feature
<222> LOCATION: (1)..(4)
<223> OTHER INFORMATION: 2'-O-methylribonucleotides
<220> FEATURE:
<221> NAME/KEY: misc_feature
<222> LOCATION: (17)..(20)
<223> OTHER INFORMATION: 2'-O-methylribonucleotides

<400> SEQUENCE: 40
cucucagtgg tgttgaggac                                                  20

<210> SEQ ID NO 41
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 41
cagcaggagc ctctcagtgg                                                  20

<210> SEQ ID NO 42
```

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 42
gtcctgatat agttgaagct                                              20

<210> SEQ ID NO 43
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 43
ggaaggatga agcagtgact                                              20

<210> SEQ ID NO 44
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 44
ctgcagctgt tccagaaagg                                              20

<210> SEQ ID NO 45
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 45
tggctcccga gctccagcag                                              20

<210> SEQ ID NO 46
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 46
caatagtcaa gggggtatac                                              20

<210> SEQ ID NO 47
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 47
gtttctgaag gcctccttgt                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 48
```
aagattctaa ggttgggcag                                                     20

<210> SEQ ID NO 49
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 49
tcttactact tcccaggtcc                                                     20

<210> SEQ ID NO 50
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 50
atctggatgc aagaagtata                                                     20

<210> SEQ ID NO 51
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 51
tggaacagtc cctgaaaagc                                                     20

<210> SEQ ID NO 52
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 52
acagtctaag ttcaaacaga                                                     20

<210> SEQ ID NO 53
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 53
atcagagaga ccacagaaat                                                     20

<210> SEQ ID NO 54
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 54
taaccatctt tcaatacagc                                                     20

<210> SEQ ID NO 55
<211> LENGTH: 20
<212> TYPE: DNA
<213> ORGANISM: Artificial Sequence
<220> FEATURE:

<223> OTHER INFORMATION: Antisense oligonucleotide

<400> SEQUENCE: 55
aagcctttaa atttctgaaa                    20

<210> SEQ ID NO 56
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 56
ggatagatcc aagcgagtta                    20

<210> SEQ ID NO 57
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 57
aggctacgaa tctgattttt                    20

<210> SEQ ID NO 58
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 58
caaatgaagg atgaaggtaa                    20

<210> SEQ ID NO 59
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 59
ctttaaggaa ttcaacttcc                    20

<210> SEQ ID NO 60
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 60
ttggaggaaa aatctatgga                    20

<210> SEQ ID NO 61
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 61
cacatacaag gaatatttgg                    20

<210> SEQ ID NO 62

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 62 tagggctcg agctcatgtt                                                   20

<210> SEQ ID NO 63
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 63
aaggagagcg ttttcccttg                                                  20

<210> SEQ ID NO 64
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 64
tattagctgc gaggctaaaa                                                  20

<210> SEQ ID NO 65
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 65
tgagactctg ctatacaagc                                                  20

<210> SEQ ID NO 66
<211> LENGTH: 20
<212> TYPE: DNA
<213> ORGANISM: Artificial Sequence
<220> FEATURE:
<223> OTHER INFORMATION: Antisense oligonucleotide
<220> FEATURE:
<221> NAME/KEY: misc_feature
<222> LOCATION: (1)..(4)
<223> OTHER INFORMATION: 2'-O-methylribonucleotides
<220> FEATURE:
<221> NAME/KEY: misc_feature
<222> LOCATION: (17)..(20)
<223> OTHER INFORMATION: 2'-O-methylribonucleotides

<400> SEQUENCE: 66
ccagtccact gagactcugc                                                  20

<210> SEQ ID NO 67
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 67
atacattttc cccagtccac                                                  20

<210> SEQ ID NO 68
```

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 68
ccatgtttct gaatgggttc                                              20

<210> SEQ ID NO 69
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 69
aacatctagt atctccagca                                              20

<210> SEQ ID NO 70
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 70
actgtccagc catttccaga                                              20

<210> SEQ ID NO 71
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 71
taaagtttcc tgtgatgtcc                                              20

<210> SEQ ID NO 72
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 72
gcttttgctg atggcattgc                                              20

<210> SEQ ID NO 73
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 73
agaatcaaag agaaggcctg                                              20

<210> SEQ ID NO 74
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 74
```

```
cacccatgat gtggtgggca                                        20
```

<210> SEQ ID NO 75
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 75

```
gttatggaag ccaaacccgg                                        20
```

<210> SEQ ID NO 76
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 76

```
ttctggtcag gatctttgat                                        20
```

<210> SEQ ID NO 77
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 77

```
tggccaggcc agcaaatgtg                                        20
```

<210> SEQ ID NO 78
<211> LENGTH: 20
<212> TYPE: DNA
<213> ORGANISM: Artificial Sequence
<220> FEATURE:
<223> OTHER INFORMATION: Antisense oligonucleotide
<220> FEATURE:
<221> NAME/KEY: misc_feature
<222> LOCATION: (1)..(4)
<223> OTHER INFORMATION: 2'-O-methylribonucleotides
<220> FEATURE:
<221> NAME/KEY: misc_feature
<222> LOCATION: (17)..(20)
<223> OTHER INFORMATION: 2'-O-methylribonucleotides

<400> SEQUENCE: 78

```
auccaggtgt ctcactgaac                                        20
```

<210> SEQ ID NO 79
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 79

```
acaaacccat gtgaaagatc                                        20
```

<210> SEQ ID NO 80
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 80

```
ctcgtgagtt cagggagaag                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 81
atccttgagt gtctcaaaga                                              20

<210> SEQ ID NO 82
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 82
gcaaggttca gaaccttcaa                                              20

<210> SEQ ID NO 83
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 83
tcttatttat cttgttgtag                                              20

<210> SEQ ID NO 84
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 84
gtaaaatgct tcatctgcaa                                              20

<210> SEQ ID NO 85
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 85
acttggaggt tgtcaagtcc                                              20

<210> SEQ ID NO 86
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 86
ggttatatga caaattgaga                                              20

<210> SEQ ID NO 87
<211> LENGTH: 20
<212> TYPE: DNA
<213> ORGANISM: Artificial Sequence
<220> FEATURE:
```

```
<223> OTHER INFORMATION: Antisense oligonucleotide

<400> SEQUENCE: 87
actgtaaagt tcccccagaa                                                    20

<210> SEQ ID NO 88
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 88
ggtagtccat agaaattcga                                                    20

<210> SEQ ID NO 89
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 89
aatcaatgta ggctacctta                                                    20

<210> SEQ ID NO 90
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 90
tgcaatgtga ttcttttgca                                                    20

<210> SEQ ID NO 91
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 91
aatgtttggt cttgaattat                                                    20

<210> SEQ ID NO 92
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 92
gtaatttttc caggaatttg                                                    20

<210> SEQ ID NO 93
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 93
gtctcggaga tccaaggtct                                                    20

<210> SEQ ID NO 94
```

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 94
tgaatggttg taagagcatt                                            20

<210> SEQ ID NO 95
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 95
cgggtatgct tggaataaaa                                            20

<210> SEQ ID NO 96
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 96
attgccactc aagaagatat                                            20

<210> SEQ ID NO 97
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 97
tttggcaaag tcactagttt                                            20

<210> SEQ ID NO 98
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 98
ggttcgctgt aaggttgatc                                            20

<210> SEQ ID NO 99
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 99
gttttctgat aagtggatga                                            20

<210> SEQ ID NO 100
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 100
```
atatctagat tttctagcct                                                20

<210> SEQ ID NO 101
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 101
cccgtaggag aaagtagaga                                                20

<210> SEQ ID NO 102
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 102
gagaatctgg agatgaggta                                                20

<210> SEQ ID NO 103
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 103
aagcgatttt gatttaaaat                                                20

<210> SEQ ID NO 104
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 104
gatctccact acaggaggag                                                20

<210> SEQ ID NO 105
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 105
gggattctct gaagggnttt                                                20

<210> SEQ ID NO 106
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 106
aggaaaagct gttctaagct                                                20

<210> SEQ ID NO 107
<211> LENGTH: 20
<212> TYPE: DNA
<213> ORGANISM: Artificial Sequence
<220> FEATURE:

<223> OTHER INFORMATION: Antisense oligonucleotide

<400> SEQUENCE: 107
gttgcaacat attttctcca        20

<210> SEQ ID NO 108
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 108
gagctcagtt tcccaggcaa        20

<210> SEQ ID NO 109
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 109
ccctcaaaaa catcccaaca        20

<210> SEQ ID NO 110
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 110
gaacttgaag atgagaaagt        20

<210> SEQ ID NO 111
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 111
atagttatga ttcaaataca        20

<210> SEQ ID NO 112
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 112
cctggtggaa gggaattaag        20

<210> SEQ ID NO 113
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 113
cagtcagatg gctaaatact        20

<210> SEQ ID NO 114

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 114
gaggcttagt ccccttaatg                                              20

<210> SEQ ID NO 115
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 115
actgtcagcc tgttggagtt                                              20

<210> SEQ ID NO 116
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 116
gtaaatcatt gtgagaaaga                                              20

<210> SEQ ID NO 117
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 117
caggatctct aaattagcag                                              20

<210> SEQ ID NO 118
<211> LENGTH: 20
<212> TYPE: DNA
<213> ORGANISM: Artificial Sequence
<220> FEATURE:
<223> OTHER INFORMATION: Antisense oligonucleotide
<220> FEATURE:
<221> NAME/KEY: misc_feature
<222> LOCATION: (1)..(4)
<223> OTHER INFORMATION: 2'-O-methylribonucleotides
<220> FEATURE:
<221> NAME/KEY: misc_feature
<222> LOCATION: (17)..(20)
<223> OTHER INFORMATION: 2'-O-methylribonucleotides

<400> SEQUENCE: 118
gcuggttcct ggatatgucc                                              20

<210> SEQ ID NO 119
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 119
catcaggatt aggagctagg                                              20

<210> SEQ ID NO 120
```

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 120
gacactaagt gatacaaata                                                 20

<210> SEQ ID NO 121
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 121
ttgttatgag ttatatccaa                                                 20

<210> SEQ ID NO 122
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 122
gttcacattc acaaatgaac                                                 20

<210> SEQ ID NO 123
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 123
ccaattgata aaagtgctaa                                                 20

<210> SEQ ID NO 124
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 124
gtgacattgg tgtgattaag                                                 20

<210> SEQ ID NO 125
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 125
ctgcaggagg cccagctata                                                 20

<210> SEQ ID NO 126
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 126
```

-continued

```
agggtacaca caatatatgt                                           20

<210> SEQ ID NO 127
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 127
gaaaccccag agaacgagtc                                           20

<210> SEQ ID NO 128
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 128
ccgtggaaag agagaagagg                                           20

<210> SEQ ID NO 129
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 129
ttcctcttca tcacaacctt                                           20

<210> SEQ ID NO 130
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 130
aactttaggg actttaagac                                           20

<210> SEQ ID NO 131
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 131
tgcatacaat gaaagggag                                            20

<210> SEQ ID NO 132
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 132
gaacagagtc agagtgacag                                           20

<210> SEQ ID NO 133
<211> LENGTH: 20
<212> TYPE: DNA
<213> ORGANISM: Artificial Sequence
<220> FEATURE:
```

```
<223> OTHER INFORMATION: Antisense oligonucleotide

<400> SEQUENCE: 133
actgtgagga tggtcatgag                                               20

<210> SEQ ID NO 134
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 134
agaagccccg gaactttgtg                                               20

<210> SEQ ID NO 135
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 135
tgtcttataa cagataaaac                                               20

<210> SEQ ID NO 136
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 136
ttgaacacca gtctctgggc                                               20

<210> SEQ ID NO 137
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 137
ctgtgccctg gggatggtcc                                               20

<210> SEQ ID NO 138
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 138
atatttgtac atatcaggtt                                               20

<210> SEQ ID NO 139
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 139
ctgaagcaca aataggcatc                                               20

<210> SEQ ID NO 140
```

```
<211> LENGTH: 20
<212> TYPE: DNA
<213> ORGANISM: Artificial Sequence
<220> FEATURE:
<223> OTHER INFORMATION: Antisense oligonucleotide
<220> FEATURE:
<221> NAME/KEY: misc_feature
<222> LOCATION: (1)..(4)
<223> OTHER INFORMATION: 2'-O-methylribonucleotides
<220> FEATURE:
<221> NAME/KEY: misc_feature
<222> LOCATION: (17)..(20)
<223> OTHER INFORMATION: 2'-O-methylribonucleotides

<400> SEQUENCE: 140
gaagtctttg ctgctgaagc                                               20

<210> SEQ ID NO 141
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 141
tttgagcaaa gcattctgca                                               20

<210> SEQ ID NO 142
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 142
ctgtattgag tgtccaggtg                                               20

<210> SEQ ID NO 143
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 143
ggttgaatct gttttggtca                                               20

<210> SEQ ID NO 144
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 144
gtctctttct tcaaagcaca                                               20

<210> SEQ ID NO 145
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 145
cggttttctc ctgggacaaa                                               20

<210> SEQ ID NO 146
```

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 146
catcctggat attggcaatg                                                    20

<210> SEQ ID NO 147
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 147
ctttctactg ttccagatgg                                                    20

<210> SEQ ID NO 148
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 148
ctgctcacaa gacaaacgat                                                    20

<210> SEQ ID NO 149
<211> LENGTH: 20
<212> TYPE: DNA
<213> ORGANISM: Artificial Sequence
<220> FEATURE:
<223> OTHER INFORMATION: Antisense oligonucleotide
<220> FEATURE:
<221> NAME/KEY: misc_feature
<222> LOCATION: (1)..(4)
<223> OTHER INFORMATION: 2'-O-methylribonucleotides
<220> FEATURE:
<221> NAME/KEY: misc_feature
<222> LOCATION: (17)..(20)
<223> OTHER INFORMATION: 2'-O-methylribonucleotides

<400> SEQUENCE: 149
cucuaaggaa gtgtctgcuc                                                    20

<210> SEQ ID NO 150
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 150
actgaaggct tcaaggcacc                                                    20

<210> SEQ ID NO 151
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 151
aagcacctgc cctgggcata                                                    20

<210> SEQ ID NO 152
```

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 152
gagcactgtt aaggtcagat                                                 20

<210> SEQ ID NO 153
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 153
cccaaccacc accatgatga                                                 20

<210> SEQ ID NO 154
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 154
aactggtact gggacaagga                                                 20

<210> SEQ ID NO 155
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 155
tgatggattg atgtttcatc                                                 20

<210> SEQ ID NO 156
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 156
ctgtttctgt acaaagcctc                                                 20

<210> SEQ ID NO 157
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 157
tcaggccacc tcaaatactg                                                 20

<210> SEQ ID NO 158
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 158
```
agccaacatc ctggagatcc        20

<210> SEQ ID NO 159
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 159
agagagttta tgaagaaacc        20

<210> SEQ ID NO 160
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 160
tctttcttta gtatctgttg        20

<210> SEQ ID NO 161
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 161
tgtctttctt cttttctttt        20

<210> SEQ ID NO 162
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 162
agtttgcaac ggaatgttat        20

<210> SEQ ID NO 163
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 163
gattaggaga tggttgctac        20

<210> SEQ ID NO 164
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 164
aagttggaaa ttgctccttt        20

<210> SEQ ID NO 165
<211> LENGTH: 20
<212> TYPE: DNA
<213> ORGANISM: Artificial Sequence
<220> FEATURE:

```
<223> OTHER INFORMATION: Antisense oligonucleotide

<400> SEQUENCE: 165
agttatttgt ggcttgagat                                               20

<210> SEQ ID NO 166
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 166
ggtgcaaata caaagtgaag                                               20

<210> SEQ ID NO 167
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 167
ggaccccaaa atgataactt                                               20

<210> SEQ ID NO 168
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 168
aaaaaaaaaa cctccagaga                                               20

<210> SEQ ID NO 169
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 169
gttttcatag tagcaaaaag                                               20

<210> SEQ ID NO 170
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 170
aaaattgaga gatttatgtt                                               20

<210> SEQ ID NO 171
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 171
cagaacatgg tgttgatacg                                               20

<210> SEQ ID NO 172
```

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 172
ccatttggag gttagtgaga                                                   20

<210> SEQ ID NO 173
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 173
ttttctagat ctattatttt                                                   20

<210> SEQ ID NO 174
<211> LENGTH: 3431
<212> TYPE: DNA
<213> ORGANISM: Homo sapiens

<400> SEQUENCE: 174
ggttttcagg agcccgagcg agggcgccgc ttttgcgtcc gggaggagcc aaccgtggcg       60
caggcggcgc ggggaggcgt cccagagtct cactctgccg cccaggctgg actgcagtga      120
cacaatctcg gctgactgca accactgcct ccagggttca agcgattctc ttgcctcagc      180
ctcccaagta gctgggatta cagattgatg ttcatgttcc tgacactact acaagattca      240
tactcctgat gctactgaca acgtggcttc tccacagtca ccaaaccagg gatgctatac      300
tggacttccc tactctcatc tgctccagcc cctgacctt atagttgccc agctttcctg       360
gcaattgact ttgcccatca atacacagga tttagcatcc agggaagatg tcggagcctc      420
agatgttaat tttctaattg agaatgttgg cgctgtccga acctggagac aggaaaacaa      480
aaagtccttt ctcctgattc accaaaaaat aaaatactga ctaccatcac tgtgatgaga      540
ttcctatagt ctcaggaact gaagtcttta acaaccagg accctctgc ccctagaata       600 agaacatact agaagtccct tctgctagga caacgaggat catgggagac cacctggacc      660
ttctcctagg agtggtgctc atggccggtc ctgtgtttgg aattccttcc tgctcctttg      720
atggccgaat agccttttat cgtttctgca acctcaccca ggtccccag gtcctcaaca      780 ccactgagag gctcctgctg agcttcaact atatcaggac agtcactgct tcatccttcc      840
cctttctgga acagctgcag ctgctggagc tcggagcca gtataccccc ttgactattg       900
acaaggaggc cttcagaaac ctgcccaacc ttagaatctt ggacctggga agtagtaaga      960
tatacttctt gcatccagat gcttttcagg gactgttcca tctgtttgaa cttagactgt     1020
atttctgtgg tctctctgat gctgtattga aagatggtta tttcagaaat ttaaaggctt     1080
taactcgctt ggatctatcc aaaaatcaga ttcgtagcct ttaccttcat ccttcatttg     1140
ggaagttgaa ttccttaaag tccatagatt tttcctccaa ccaaatattc cttgtatgtg     1200
aacatgagct cgagccccta caagggaaaa cgctctcctt ttttagcctc gcagctaata     1260
gcttgtatag cagagtctca gtggactggg gaaaatgtat gaacccattc agaaacatgg     1320
tgctggagat actagatgtt tctggaaatg gctggacagt ggacatcaca ggaaactta      1380 gcaatgccat cagcaaaagc caggccttct ctttgattct tgcccaccac atcatgggtg     1440
ccgggtttgg cttccataac atcaaagatc ctgaccagaa cacatttgct ggcctggcca     1500
```

```
gaagttcagt gagacacctg gatctttcac atgggtttgt cttctccctg aactcacgag   1560
tctttgagac actcaaggat ttgaaggttc tgaaccttgc ctacaacaag ataaataaga   1620
ttgcagatga agcattttac ggacttgaca acctccaagt tctcaatttg tcatataacc   1680
ttctggggga actttacagt tcgaatttct atggactacc taaggtagcc tacattgatt   1740
tgcaaaagaa tcacattgca ataattcaag accaaacatt caaattcctg gaaaaattac   1800
agaccttgga tctccgagac aatgctctta caaccattca ttttattcca agcatacccg   1860
atatcttctt gagtggcaat aaactagtga ctttgccaaa gatcaacctt acagcgaacc   1920
tcatccactt atcagaaaac aggctagaaa atctagatat tctctacttt ctcctacggg   1980
tacctcatct ccagattctc attttaaatc aaaatcgctt ctcctcctgt agtggagatc   2040 aaacccttc agagaatccc agcttagaac agcttttcct tggagaaaat atgttgcaac    2100
ttgcctggga aactgagctc tgttgggatg tttttgaggg actttctcat cttcaagttc   2160
tgtatttgaa tcataactat cttaattccc ttccaccagg agtatttagc catctgactg   2220
cattaagggg actaagcctc aactccaaca ggctgacagt tctttctcac aatgatttac   2280
ctgctaattt agagatcctg gacatatcca ggaaccagct cctagctcct aatcctgatg   2340
tatttgtatc acttagtgtc ttggatataa ctcataacaa gttcatttgt gaatgtgaac   2400
ttagcacttt tatcaattgg cttaatcaca ccaatgtcac tatagctggg cctcctgcag   2460
acatatattg tgtgtaccct gactcgttct ctggggtttc cctcttctct ctttccacgg   2520
aaggttgtga tgaagaggaa gtcttaaagt ccctaaagtt ctcccttttc attgtatgca   2580
ctgtcactct gactctgttc ctcatgacca tcctcacagt cacaaagttc cggggcttct   2640
gttttatctg ttataagaca gcccagagac tggtgttcaa ggaccatccc cagggcacag   2700
aacctgatat gtacaaatat gatgcctatt tgtgcttcag cagcaaagac ttcacatggg   2760
tgcagaatgc tttgctcaaa cacctggaca ctcaatacag tgaccaaaac agattcaacc   2820
tgtgctttga agaaagagac tttgtcccag gagaaaaccg cattgccaat atccaggatg   2880
ccatctggaa cagtagaaag atcgtttgtc ttgtgagcag acacttcctt agagatggct   2940
ggtgccttga agccttcagt tatgcccagg gcaggtgctt atctgacctt aacagtgctc   3000
tcatcatggt ggtggttggg tccttgtccc agtaccagtt gatgaaacat caatccatca   3060
gaggctttgt acagaaacag cagtatttga ggtggcctga ggatctccag gatgttggct   3120
ggtttcttca taaactctct caacagatac taaagaaaga aaaagaaaag aagaaagaca   3180
ataacattcc gttgcaaact gtagcaacca tctcctaatc aaaggagcaa tttccaactt   3240
atctcaagcc acaaataact cttcactttg tatttgcacc aagttatcat tttggggtcc   3300
tctctggagg ttttttttt cttttgcta ctatgaaaac aacataaatc tctcaatttt    3360
cgtatcaaca ccatgttctg tctcactaac ctccaaatgg aaaataatag atctagaaaa   3420
ttgcaactgc c                                                       3431
```